(12) United States Patent
Gogoana et al.

(10) Patent No.: US 11,054,347 B1
(45) Date of Patent: Jul. 6, 2021

(54) ENHANCED GAS SENSOR SELECTIVITY

(71) Applicant: X Development LLC, Mountain View, CA (US)

(72) Inventors: Radu Gogoana, Burlingame, CA (US); Neil David Treat, San Jose, CA (US)

(73) Assignee: X Development LLC, Mountain View, CA (US)

( * ) Notice: Subject to any disclaimer, the term of this patent is extended or adjusted under 35 U.S.C. 154(b) by 0 days.

(21) Appl. No.: 16/732,282

(22) Filed: Dec. 31, 2019

(51) Int. Cl.
  *G01N 1/22* (2006.01)
  *G01N 1/24* (2006.01)
  *G01N 7/10* (2006.01)
  *G01N 33/00* (2006.01)
  *G01N 1/40* (2006.01)
  *G01N 1/26* (2006.01)

(52) U.S. Cl.
  CPC .............. *G01N 1/2214* (2013.01); *G01N 1/24* (2013.01); *G01N 1/405* (2013.01); *G01N 7/10* (2013.01); *G01N 33/0011* (2013.01); *G01N 33/0047* (2013.01); *G01N 1/26* (2013.01); *G01N 2001/4016* (2013.01)

(58) Field of Classification Search
  CPC ........ G01N 7/10; G01N 1/24; G01N 33/0011; G01N 1/405; G01N 33/0047; G01N 2001/4016
  USPC ....................................................... 73/31.07
  See application file for complete search history.

(56) References Cited

U.S. PATENT DOCUMENTS

| | | | | |
|---|---|---|---|---|
| 3,970,012 A | * | 7/1976 | Jones, Sr. ............... | A01B 21/04 111/118 |
| 4,670,405 A | * | 6/1987 | Stetter .................... | G01N 30/78 422/98 |
| 4,834,194 A | * | 5/1989 | Manchak, Jr. ........... | B09C 1/06 166/250.01 |
| 5,140,845 A | * | 8/1992 | Robbins ............... | G01N 1/2226 73/19.03 |

(Continued)

FOREIGN PATENT DOCUMENTS

| | | |
|---|---|---|
| CN | 107478590 | 12/2017 |
| CN | 107478683 | 12/2017 |

(Continued)

OTHER PUBLICATIONS

Paolo Montuschi, The Electronic Nose in Respiratory Medicine, Karger, Respiration 2013; 85:72-84, Sep. 25, 2012 (Year: 2012).*

(Continued)

*Primary Examiner* — Clayton E. LaBalle
*Assistant Examiner* — Kevin C Butler
(74) *Attorney, Agent, or Firm* — Fish & Richardson P.C.

(57) ABSTRACT

Systems and apparatus for gas sensing including: a sample inlet; a first sorbent tube and a second sorbent tube each in fluidic communication with the sample inlet, wherein the first sorbent tube is sensitive to a first set of gas analytes and the second sorbent tube is sensitive to a second, different set of gas analytes; an array of gas sensors housed in a chamber that is in fluidic communication with the first sorbent tube and the second sorbent tube; and a desorption system configured to selectively desorb and direct contents from each of the first sorbent tube and the second sorbent tube into the chamber housing the array of gas sensors at different times. Methods for gas sensing are also disclosed.

20 Claims, 14 Drawing Sheets

(56) References Cited

U.S. PATENT DOCUMENTS

| | | | | |
|---|---|---|---|---|
| 5,675,070 | A * | 10/1997 | Gelperin | G01N 33/0011 73/23.34 |
| 5,801,297 | A * | 9/1998 | Mifsud | G01N 33/14 73/23.34 |
| 6,085,576 | A | 7/2000 | Sunshine et al. | |
| 6,422,061 | B1 * | 7/2002 | Sunshine | G01N 29/022 340/603 |
| 6,455,003 | B1 * | 9/2002 | Anvia | G01N 1/40 422/88 |
| 6,914,220 | B2 * | 7/2005 | Tian | F27B 17/0025 219/385 |
| 7,827,847 | B2 * | 11/2010 | Oishi | G01N 27/16 73/23.2 |
| 8,542,024 | B2 | 9/2013 | Potyrailo et al. | |
| 9,140,677 | B2 * | 9/2015 | Mershin | G01N 33/0031 |
| 9,341,604 | B2 * | 5/2016 | Fan | G01N 30/465 |
| 9,737,920 | B2 * | 8/2017 | Winzeler | B01D 1/0094 |
| 9,823,211 | B1 * | 11/2017 | Allen | G01N 33/0031 |
| 1,033,062 | A1 | 6/2019 | Tayebi et al. | |
| 1,033,195 | A1 | 6/2019 | Ahn et al. | |
| 10,321,851 | B2 * | 6/2019 | Weda | A61M 16/1045 |
| 10,330,624 | B2 * | 6/2019 | Tayebi | G01N 27/124 |
| 10,331,954 | B2 * | 6/2019 | Ahn | G01N 33/0073 |
| 2002/0124631 | A1 * | 9/2002 | Sunshine | G01N 33/0009 73/23.2 |
| 2004/0101851 | A1 * | 5/2004 | White | C12Q 1/6825 435/6.19 |
| 2005/0288183 | A1 * | 12/2005 | Sandra | G01N 1/40 502/407 |
| 2006/0120919 | A1 * | 6/2006 | Aslam | G01N 30/08 422/69 |
| 2006/0191319 | A1 * | 8/2006 | Kurup | G01N 33/24 73/23.34 |
| 2008/0008625 | A1 * | 1/2008 | Thomas | G01N 21/3504 422/82.05 |
| 2008/0028827 | A1 * | 2/2008 | Andrews | G01N 1/2294 73/23.2 |
| 2009/0040044 | A1 | 2/2009 | Chiao et al. | |
| 2009/0261987 | A1 * | 10/2009 | Sun | G01N 27/414 340/870.07 |
| 2010/0137733 | A1 * | 6/2010 | Wang | A61B 5/08 600/532 |
| 2011/0067572 | A1 * | 3/2011 | Rogers | B01D 53/0446 96/147 |
| 2012/0270205 | A1 * | 10/2012 | Patel | G01N 27/126 435/5 |
| 2012/0270334 | A1 * | 10/2012 | Ojeda | G01N 27/622 436/178 |
| 2013/0211207 | A1 | 8/2013 | Joseph et al. | |
| 2015/0323510 | A1 | 11/2015 | Huynh et al. | |
| 2016/0266084 | A1 * | 9/2016 | Burge | G01N 33/1826 |
| 2016/0341697 | A1 * | 11/2016 | Lal | G01N 27/62 |
| 2017/0082586 | A1 * | 3/2017 | Williamson | G01N 33/0022 |
| 2017/0292368 | A1 * | 10/2017 | Irani | E21B 47/113 |
| 2018/0003660 | A1 | 1/2018 | Tayebi et al. | |
| 2018/0088092 | A1 * | 3/2018 | Knight | G01N 1/2214 |
| 2018/0110444 | A1 * | 4/2018 | Sherwood | A61B 5/08 |
| 2018/0128791 | A1 * | 5/2018 | Knight | G01N 1/405 |
| 2018/0237294 | A1 * | 8/2018 | Giordano | G01N 27/4146 |
| 2019/0167152 | A1 * | 6/2019 | Weda | G16H 50/20 |

FOREIGN PATENT DOCUMENTS

| | | | |
|---|---|---|---|
| KR | 101700244 | 1/2017 | |
| WO | WO2012018591 | 2/2012 | |
| WO | WO-2012018591 A1 * | 2/2012 | G01N 33/0031 |
| WO | WO 2019/018137 | 1/2019 | |

OTHER PUBLICATIONS

Xuntao Xu et al., A Solid Trap and Thermal Desorption System with Application to a Medical Electronic Nose, Sensors 2008, 6885-6898 (Year: 2008).*

MP van der Schee et al., Effect of transportation and storage using sorbent tubes of exhaled breath samples on diagnostic accuracy of electronic nose analysis, IOP Publishing, Dec. 21, 2012, 7 pgs (Year: 2012).*

De Vito et al, "On field calibration of an electronic nose for benzene estimation in an urban pollution monitoring scenario," in Sensors and Actuatiors B: Chemical, Science Direct, Feb. 22, 2008, 8 pages.

Holmberg et al, "Drift counteraction in odour recognition applications: lifelong calibration method," in Sensors and Actuators B: Chemical, Science Direct, Aug. 1997, 10 pages.

Kim et al, "A weighted-adjusted voting algorithm for ensembles of classifiers," in Journal of Korean Statistical Society, Science Direct, Dec. 2011, 13 pages.

Levitin et al, "Evaluating correct classification probability for weighted voting classifiers with plurality voting," in European Journal of Operational Research, Science Direct, Sep. 16, 2002, 12 pages.

Loutfi et al., "Object recognition: A new application for smelling robots," Robotics and Autonomous Systems, Sep. 2005, 52(4):18 pages.

Loutfi et al., "Odor Recognition for Intelligent Systems," retrieved from URL <http://citeseerx.ist.psu.edu/viewdoc/download?doi=10.1.1.139.8681&rep=rep1&type=pdf>, May 2006, 19 pages.

Loutfi et al., "Putting Olfaction into Action: Using an Electronic Nose on a Multi-Sensing Mobile Robot," 2004 IEEE/RSJ International Conference on Intelligent Robots and Systems (IROS), Sep. 2004, 6 pages.

Mallin, "Increasing the Selectivity and Sensitivity of the Gas Sensors for the Detection of Explosives," 2014, Semantic Scholar, 166 pages.

Phaisangittisagul et al, "Intelligent method for sensor subset selection for machine olfaction," ScienceDirect, Mar. 2010, 507-515.

Bur, "Selectivity Enhancement of Gas Sensitive Field Effect Transistors by Dynamic Operation," Dissertation No. 1644, Linkoping University Institute of Technology, 2015, 307 pages.

Cargnello et al., "Multiwalled Carbon Nanotubes Drive the Activity of Metaloxide Core-Shell Catalysts in Modular Nanocomposites," J. Am. Chem. Soc., 2012, 134:11760-11766.

Chen et al., "The enhanced ethanol sensing properties of multi-walled carbon nanotubes/SnO2core/shell nanostructures." Nanotechnology, 2006, 17:3012-3017.

Espinosa et al., "Hybrid metal oxide and multiwall carbon nanotube films for low temperature gas sensing," Sensors and Actuators B, 2007, 127:137-142.

Liu et al., "Hysteresis modeling in ballistic carbon nanotube field-effect transistors," Nanotechnology, Science and Applications. Jul. 2014, 4(7):55-61.

Mallakpour et al., "Carbon nanotube- metal oxide nanocomposites: Fabrication, properties and applications," Chemical Engineering Journal, 2016, 302:344-367.

Mirzaei et al., "Metal-coremetal oxide-shell nanomaterials for gas-sensing applications: a review," J Nanopart Res., 2015, 17(371): 36 pages.

PCT International Search Report and Written Opinion in International Appln. No. PCT/US20/52197, dated Feb. 9, 2021, 21 pages.

PCT Invitation to Pay Additional Fees in International Appln. No. PCT/US20/52197, dated Nov. 19, 2020, 2 pages.

* cited by examiner

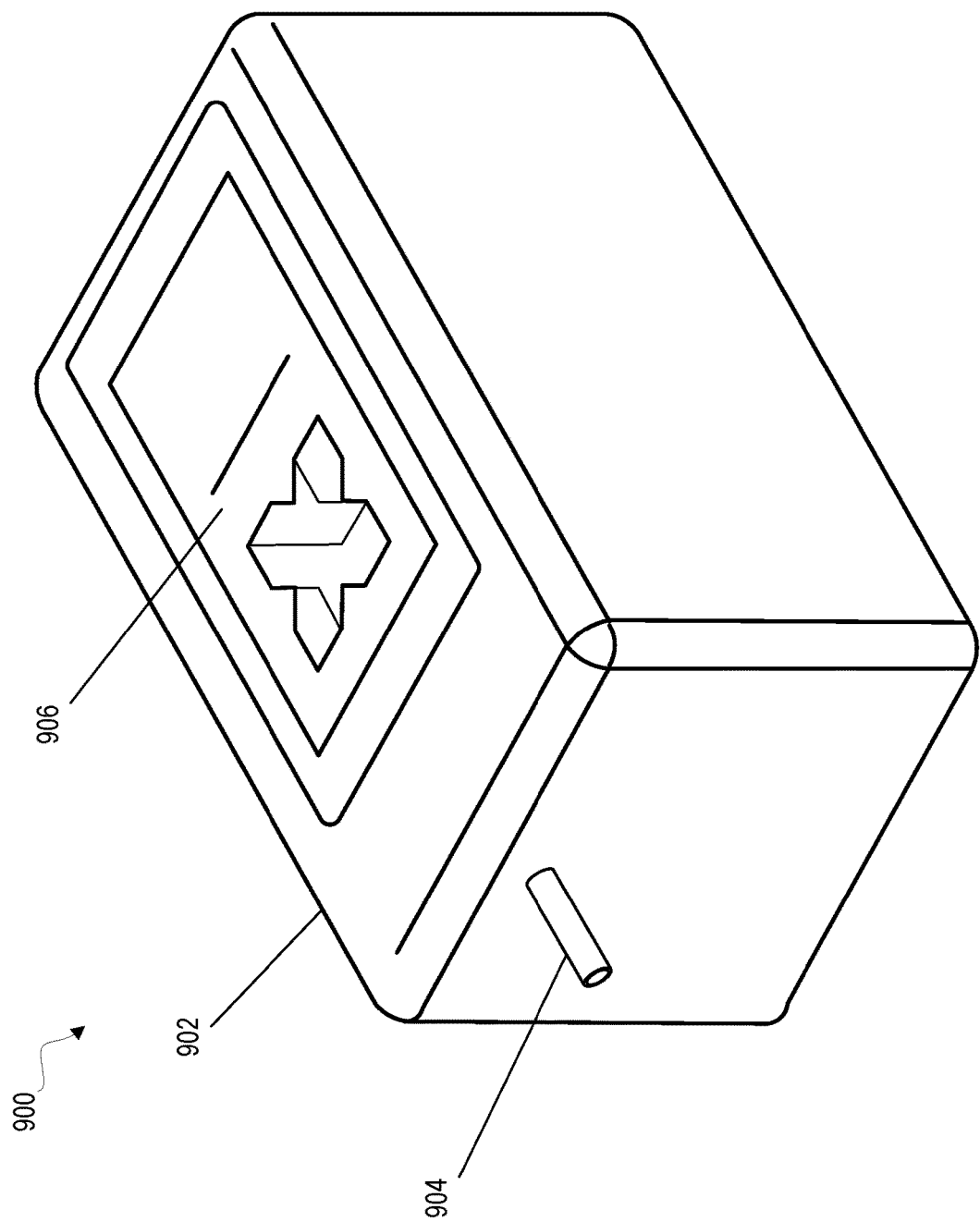

ENHANCED GAS SENSOR SELECTIVITY

BACKGROUND

Gas sensor arrays can be used to detect the presence of analytes in ambient environments surrounding the gas sensors. Detecting particular analytes in an ambient environment, e.g., volatile organic compounds can be useful for safety, manufacturing, and/or environmental monitoring applications. Individual gas sensors can be differently sensitized to a particular subset of analytes and nonreactive to other analytes.

SUMMARY

This specification describes systems, methods, devices, and other techniques relating to pre-filtering gas samples for a gas sensing apparatus. Specifically, implementations are directed to a sorbent tube array for a gas sensing apparatus and operations of the gas sensing apparatus for employing the sorbent tube array to pre-filter gas samples. For example, a gas sensing apparatus can employ an array of different sorbent tubes to enhance the selectivity of electronic gas sensors in the apparatus to distinguish between different analytes in gas samples. In some examples, a gas sensing apparatus can improve the selectivity of electronic gas sensors by passing a gas sample through several different sorbent tubes. Each sorbent tube is sensitive to a different set of gas analytes. The gas sensing apparatus individually desorbs the contents (e.g., desorbed analytes) of each sorbent tube and passes the desorbed contents to gas sensors. The array of sorbent tubes serves as an analyte selective pre-filter for the gas sensing apparatus. The contents of each sorbent tube are individually desorbed and passed to an array of gas sensors, which reduces the likelihood of one type of analyte masking another. The sorbent tubes can be removable from the gas sensing apparatus, allowing for in-situ configuration of a pre-filter to particular sets of analytes, for example.

In general, in a first aspect, the disclosure features a gas sensing apparatus including: a sample inlet; a first sorbent tube and a second sorbent tube each in fluidic communication with the sample inlet, wherein the first sorbent tube is sensitive to a first set of gas analytes and the second sorbent tube is sensitive to a second, different set of gas analytes; an array of gas sensors housed in a chamber that is in fluidic communication with the first sorbent tube and the second sorbent tube; and a desorption system configured to selectively desorb and direct contents from each of the first sorbent tube and the second sorbent tube into the chamber housing the array of gas sensors at different times.

Implementations of the gas sensing apparatus can include one or more of the following features and/or features of other aspects. For example, the desorption system can include a first flow path between the first sorbent tube and the chamber housing the array of gas sensors, and a second flow path between the second sorbent tube and the chamber containing the array of gas sensors, and wherein the gas sensing system further includes: a pump in fluidic communication with the first sorbent tube and the second tube; and a processing system configured to control operations of the gas sensing system and to perform operations that include: causing the pump to draw a gas sample through the first sorbent tube and the second sorbent tube; causing the desorption system to open the first flow path; causing the desorption system to desorb a content of the first sorbent tube into the chamber through the first flow path; obtaining, from the array of gas sensors, first sensor response data responsive to the content of the first sorbent tube; causing the desorption system to isolate the first flow path; causing the desorption system to open the second flow path; causing the desorption system to desorb a content of the second sorbent tube into the chamber; and obtaining, from the array of gas sensors, second sensor response data responsive to the content of the second sorbent tube. The operations can further include: obtaining data identifying the first set of gas analytes that the first sorbent tube is sensitive to; and identifying, based on the data identifying the first set of gas analytes and the first sensor response data, at least one analyte present in the gas sample. Identifying the at least one analyte present in the gas sample can include comparing the first sensor response data with training data from sensor response curves associated with the first set of gas analytes.

Causing the desorption system to desorb the content of the first sorbent tube can include activating a desorption mechanism associated with the first sorbent tube. Activating a desorption mechanism associated with the first sorbent tube can include activating a heater proximate to the first sorbent tube.

In some embodiments, the array of gas sensors includes a multi-modal array of gas sensors of different types.

The array of gas sensors can include a first array of gas sensors housed in a first chamber and a second array of different gas sensors house in a second chamber, and wherein the desorption system is configured to direct contents from the first sorbent tube to the first chamber and to direct contents from the second sorbent tube to the second chamber.

The desorption system can be configured to flush the chamber after desorbing and directing the contents from one of the first or second sorbent tube into the chamber.

The the first sorbent tube can be removable from the gas sensing system.

In general, in another aspect, the disclosure features a method of detecting analytes in gas, the method including: drawing a gas sample through a first sorbent tube and a second sorbent tube of a gas sensing system, wherein the first sorbent tube is sensitive to a first set of gas analytes and the second sorbent tube is sensitive to a second, different set of gas analytes; opening a first flow path between the first sorbent tube and a chamber containing an array of gas sensors; desorbing a content of the first sorbent tube into the chamber through the first flow path; obtaining, from the array of gas sensors, first sensor response data responsive to the content of the first sorbent tube; isolating the first flow path; opening a second flow path between the second sorbent tube and the chamber containing the array of gas sensors; desorbing a content of the second sorbent tube into the chamber through the second flow path; and obtaining, from the array of gas sensors, second sensor response data responsive to the content of the second sorbent tube.

Implementations of the method can include one or more of the following features and/or features of other aspects. For example, the array of gas sensors can include a multi-modal array of gas sensors of different types.

The array of gas sensors can include a first array of gas sensors housed in a first chamber and a second array of different gas sensors house in a second chamber, and wherein the first flow path directs the content from the first sorbent tube to the first chamber and the second flow path directs contents from the second sorbent tube to the second chamber.

The method can include flushing the chamber after desorbing the content of the first sorbent tube into the chamber through the first flow path.

The first sorbent tube can be removable from the gas sensing system.

The method can include: obtaining data identifying the first set of gas analytes that the first sorbent tube is sensitive to; and identifying, based on the data identifying the first set of gas analytes and the first sensor response data, at least one analyte present in the gas sample. Identifying the at least one analyte present in the gas sample can include comparing the first sensor response data with training data from sensor response curves associated with the first set of gas analytes.

Desorbing the content of the first sorbent tube can include activating a desorption mechanism associated with the first sorbent tube. Activating a desorption mechanism associated with the first sorbent tube can include activating a heater proximate to the first sorbent tube.

In general, in another aspect, the disclosure features a gas sensing system including: a sorbent tube array including a first sorbent tube and a second sorbent tube, each in fluidic communication with one or more gas sensors, wherein the first sorbent tube is sensitive to a first set of gas analytes and the second sorbent tube is sensitive to a second, different set of gas analytes; at least one processor in communication with the gas sensors; and a data store coupled to the at least one processor having instructions stored thereon which, when executed by the at least one processor, causes the at least one processor to perform operations comprising: causing a gas sample to be drawn through the first sorbent tube and the second sorbent tube; opening a first flow path between the first sorbent tube and a chamber containing the gas sensors; causing a content of the first sorbent tube to be desorbed into the chamber through the first flow path; obtaining, from the gas sensors, first sensor response data responsive to the content of the first sorbent tube; causing the first flow path to be isolated; opening a second flow path between the second sorbent tube and the chamber containing the gas sensors; causing a content of the second sorbent tube to be desorbed into the chamber through the second flow path; and obtaining, from the gas sensors, second sensor response data responsive to the content of the second sorbent tube.

Implementations of the gas sensing system can include one or more features of other aspects.

Particular embodiments of the subject matter described in this specification can be implemented so as to realize one or more of the following advantages. For example, an advantage of this technology is that it can improve the selectivity of gas sensors to distinguishing between different analytes in a gas sample. Another advantage of this technology is that it allows for the development of fully-customizable gas sensor arrays for a particular set of gases unique to a use-case by using an automated simulation of environmental variables in a controlled laboratory setting. The custom "e-nose" system can be generated from a multi-modal system generic to many different use cases and using automated sample collection and analysis, where a machine-learned model for a particular use-case is trained in the controlled environment. Additionally, a custom sub-set of gas sensors can be selected from the multi-modal generic system to create a best-fit e-nose for the particular use-case. Rather than requiring the creation of the custom device prior to collecting the data and training the model for the particular use-case, a custom sensor array can be created in real-time using the generic multi-modal sensor array and custom software feedback loops. An automated high-throughput system allows for the collection of massive amounts of pertinent odor data for the particular use-case and enables the e-nose system to properly classify odors automatically in the field.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIG. 9A-9D are schematics of example views of e-nose gas sensing apparatuses.

Like reference numbers and designations in the various drawings indicate like elements.

DETAILED DESCRIPTION

Overview

The technology of this patent application utilizes a pre-filtering sorbent tube array in a gas sensing apparatus to enhance the selectivity of the apparatus's electronic gas sensor(s). A gas sensing system employs an array of different sorbent tubes to enhance the selectivity of electronic gas sensors in distinguishing between different analytes in a gas sample. For example, a gas sensing system can improve the selectivity of electronic gas sensors by passing a gas sample through several different sorbent tubes, each being sensitive to a different set of gas analytes. The sorbent tubes can serve as a pre-filter for the gas sample. The gas sensing system individually desorbs the contents (e.g., desorbed analytes) of each sorbent tube and passes the desorbed contents to gas sensors. The array of sorbent tubes forms an analyte selective pre-filter to the gas sensing system. The tubes can be selected to pre-filter and concentrate particular sets of analytes. The contents of each sorbent tube are individually desorbed and passed to an array of gas sensors, which reduces the likelihood of one type of analyte masking another.

The sorbent tubes can be removable. For example, the sorbent tubes can be readily replaced when exhausted. The removable sorbent tubes also permits the array to be reconfigured to pre-filter specific sets of analytes and improve the selectivity of an array of gas sensor to the particular analytes of interest in a given situation.

In one example, a gas sensing system includes an array of at least two different sorbent tubes positioned between a gas sample inlet and a chamber housing the gas sensors. The gas sensing system also includes a desorption system that is configured to control the desorption of the contents from each sorbent tube and individually provide the desorbed contents into the chamber housing the gas sensors. For example, the desorption system can include an array of controllable valves separating the sorbent tube outlets from the sensor chamber. The controllable values are controlled to selectively open individual flow paths between each sorbent tube and the chamber, allowing the contents of each sorbent tube to be separately desorbed and passed into the chamber of gas sensors. In some examples, the analyte array and desorption system can be implemented as a separate attachment to a gas sensing system.

E-Nose Multi-Modal Gas Sensing Array Training Environment

Figure 1:
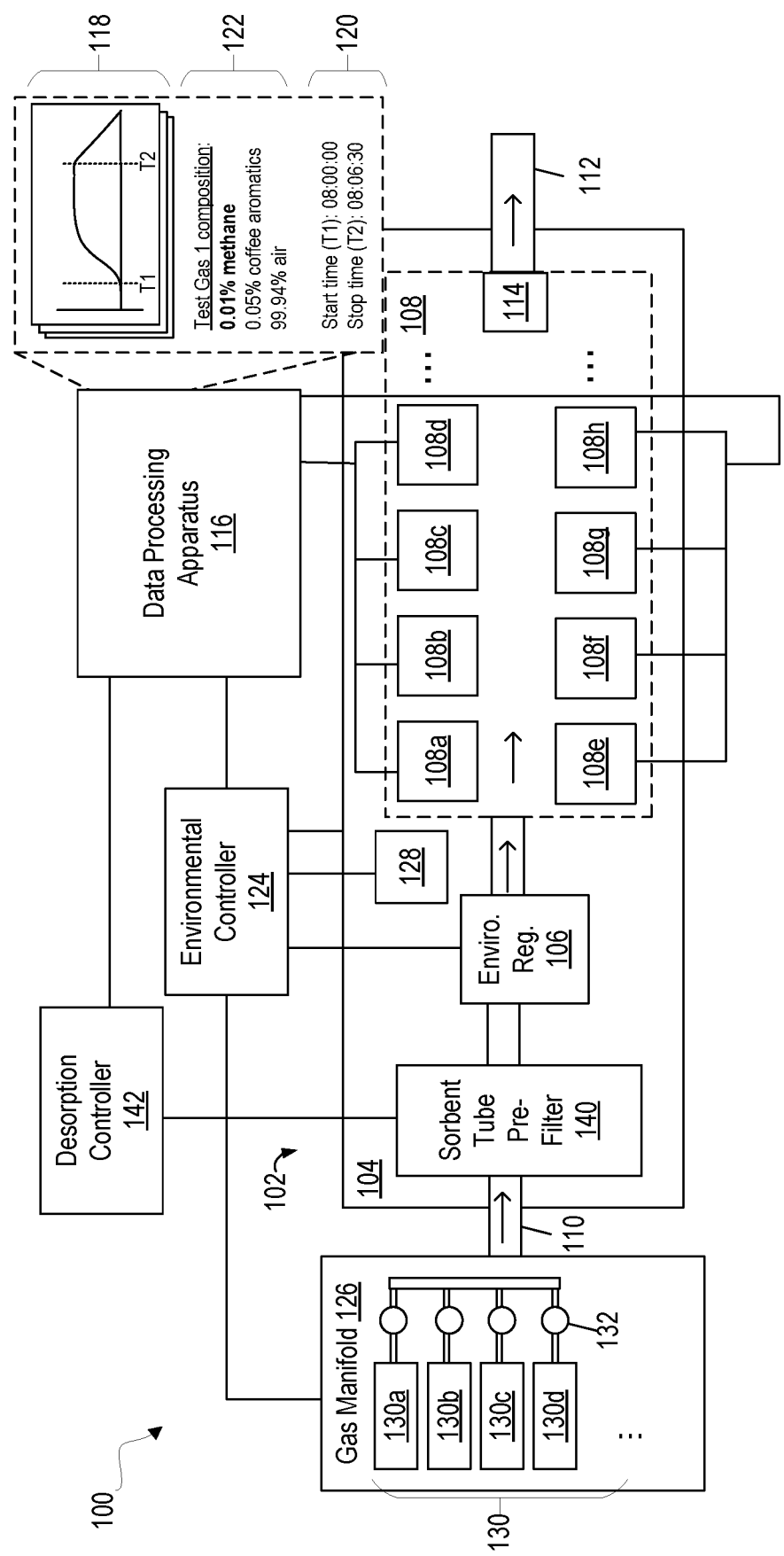
FIG. 1 is a block diagram of an example system for training an e-nose gas sensing apparatus.

FIG. 1 is a block diagram of an example system 100 for training an e-nose gas sensing apparatus 102. The system 100 for training an e-nose gas sensing apparatus 102 can include a controlled environment, e.g., a laboratory setting, where external environmental factors, e.g., temperature, humidity, presence of chemicals/gases, is highly controlled and/or regulated.

The gas sensing apparatus 102 includes a housing 104 including an environment regulator 106 and sorbent tube pre-filter 140. Environmental regulator 106 can include a heat-exchange component, e.g., cylindrical heaters inserted into the housing, and/or heat transfer fins for controlling the temperature of gases that are introduced through the gas inlet 110. The heat-exchange component can be configured to interact with the gas and regulate a temperature of the gas to the particular temperature and prior to entering the gas inlet.

Environmental regulator 106 can be configured to control a temperature within the housing 104, gas sensors 108, and a gas within the housing 104, for example, to a temperature between 40-45° C., to a temperature above dew point >16° C., or at a temperature relevant to an environment of interest (e.g., room temperature 23° C.). In some implementations, environmental regulator 106 can be configured to regulate a relative humidity within the housing 104, gas sensors 108, and a gas within the housing 104, e.g., to a relative humidity below 10%, to a relative humidity between 10-30%, or to a relative humidity relevant to an environment of interest.

The housing 104 and environmental regulator 106 can be in thermal contact such that the gas introduced through the gas inlet 110, the gas sensors 108, and the housing 104 are all maintained at a same temperature during operation of the apparatus 102.

Sorbent tube pre-filter system 140 can be configured to pre-filter various different analyses or sets of analytes from a test gas sample prior to passing the test gas to a set of gas sensors 108 for analysis. Sorbent tube pre-filter system 140 can be integrated into the housing 104 of a gas sensing apparatus 102 (as illustrated). In some examples, sorbent tube pre-filter system 140 can be implemented as a separate pre-filtering apparatus. In such examples, sorbent tube pre-filter system 140 can be installed between the gas manifold 126 and the gas inlet 110, for example. As discussed in more detail below, sorbent tube pre-filter system 140 includes an array of multiple different sorbent tubes and a desorption system to individually desorb and pass the content of each sorbent tube to the gas sensors 108. Gas sensors 108 are disposed inside a chamber. In some implementations, the housing 104 can serve as the chamber. In some implementations, the gas sensors 108 are disposed in a chamber separate from the housing 104. For example, different sets of sensors 108 can each be disposed in one of multiple separate chambers within the housing 104. Such a configuration may allow for separate analysis of the content from two different sorbent tubes at a time.

Sorbent tube pre-filter system 140 is configured to separate different analytes or sets of analytes from a gas into an array of different sorbent tubes, and separately desorb and pass the individual analytes (or sets of analytes), i.e., the content of each sorbent tube, to the gas sensors 108. In other words, the sorbent tube pre-filter system 140 forms an analyte selective pre-filter for the gas sensing apparatus that can serve to disambiguate output from gas sensor(s) 108 that might be responsive to multiple different analytes. For example, a particular one of the gas sensors 108 may produce a similar output when in the presence of two different analytes (e.g., methanol and ethanol). The sorbent tube pre-filter system 140 may permit disambiguation between methanol and ethanol without changing the operation of the sensor. For instance, sorbent tube pre-filter system 140 can include a first sorbent tube that adsorb methanol and a second sorbent tube that adsorb ethanol. A test gas is passed through both sorbent tubes and the content of each tube is then separately desorbed and passed to the gas sensor 108. If the gas sensor 108 generates a positive response when in the presence of the desorbed content from the first sorbent tube and a negative response when in the present of the desorbed content from the second sorbent tube, the gas sensing apparatus can determine that the test gas contains methanol and does not contain ethanol. If the gas sensor 108 generates a negative response when in the presence of the desorbed content from the first sorbent tube and a positive response when in the present of the desorbed content from the second sorbent tube, the gas sensing apparatus can determine that the test gas contains ethanol and does not contain methanol. If the gas sensor 108 generates a positive response when in the presence of the desorbed content from the first sorbent tube and a positive response when in the present of the desorbed content from the second sorbent tube, the gas sensing apparatus can determine that the test gas contains both methanol and ethanol. The sorbent tube pre-filter system 140 is discussed in more detail below with reference to FIGS. 5 and 6.

Housing 104 can be composed of various materials that are selected to be non-reactive to a set of analytes to which the housing 104 will be exposed. Materials for the housing 104 can include, for example, Teflon, Teflon-coated aluminum or stainless steel, Delrin, or other materials that are resistant to the set of analytes.

Housing 104 includes fixtures to hold a set of gas sensors 108 within the housing 104. The fixtures can be configured to accommodate particular dimensions of the gas sensors, and a layout of the fixtures within the housing 104 can be configured to designate particular locations for different types of gas sensors 108 within the housing 104.

Housing 104 further includes a gas inlet 110 and a gas outlet 112, where the gas inlet 110 is configured to allow for the introduction of gases into the housing 104 and to flow gas across the gas sensors 108. Gas outlet 112 is configured to allow for the purge of the gases from the housing 104.

Gas inlet 110 and gas outlet 112 can be configured for gas flow rates ranging between 0-10 cubic feet/hour, e.g., 5 cubic feet/hour. A particular flow rate for a gas into the gas inlet 110 can be selected, for example, based on an amount of time it takes for the environmental regulator 106 to bring a gas introduced at the gas inlet 110 to a test temperature, e.g., how long the gas will have to be in the fins to get it to the temperature of the housing 104.

In some implementations, gas sensing apparatus 102 includes a fan 114 configured to generate a negative pressure at the gas inlet 110 and within the housing 104 which can draw a gas into the housing 104 via the gas inlet 110, move the gas across the gas sensors 108, and purge the gas from the gas outlet 112. One or more operating parameters of the fan 114, e.g., a rotational speed of the fan, can be selected to regulate a desired flow rate of the gas through the gas sensing apparatus 102.

Gas sensors 108 include a multi-modal array of gas sensors that can be sensitive to various different organic and/or inorganic compounds. In other words, the multi-modal array of gas sensors 108 can include gas sensors that are responsive to certain analytes in a test gas and not sensitive to others. Types of gas sensors 108 can include gas sensors having different sensing mechanisms, e.g., metal oxide (MOx) sensors, photoionization detector (PID) sensors, electrochemical sensors, nondispersive infrared (NDIR) sensors, or other types of gas sensors. For example, gas sensors included in a gas sensing apparatus 102 include MOx sensors 108a-c, PID sensors 108d-f, electrochemical sensor 108g, and NDIR sensor 108h.

In some implementations, types of gas sensors 108 include gas sensors having a same sensing mechanism, e.g., oxidation-based, resistivity-based, optical-based, etc., but can have different sensitivities to the multiple analytes. In other words, a first type of gas sensor 108a and a second type of gas sensor 108b have a same mechanism for gas sensing, e.g., MOx sensors that make resistivity-based measurements, but are configured to have different performance parameters, e.g., a MOx sensor operating at a first voltage bias and a MOx sensor operating at a second voltage bias, such that the respective sensitivities to certain analytes are different.

The multi-modal array of gas sensors 108 can include multiple gas sensors, e.g., 38 total gas sensors, 25 total gas sensors, greater than 40 total gas sensors. A number of each type of gas sensor relative to respective numbers of each other type of gas sensor included in the multi-modal array of gas sensors 108 can depend in part on dimensional/size considerations, cost-benefit of each type of sensor, responsivity, signal-to-noise ratio of each sensor, or the like. A field of application of the sensor array, e.g., agricultural, industrial, etc., can determine a number of each time of gas sensor relative to a respective number of each other type of gas sensor in the multi-modal array of gas sensors 108. For example, for applications that may have a fainter signal-to-noise ratio, e.g., more background analytes not of interest, more sensors will be included overall in the multi-modal array of gas sensors 108.

In some implementations, multiple different gas sensors can each have a same sensitivity to a particular analyte, e.g., a first type of gas sensor and a second type of gas sensor can each be sensitive to the particular analyte. For example, The array of gas sensors 108 can be configured within the house 104 such that a test gas introduced via an inlet 110 can be sampled simultaneously by all of the gas sensors 108 in the array of gas sensors. In other words, the test gas is exposed to the multiple gas sensors in the array of gas sensors simultaneously such that data collection from each of the multiple gas sensors 108 can be performed in parallel.

In some implementations, the multi-modal array of gas sensors can include multiple MOx sensors 108a-c that are each configured to operate at a different temperature, e.g., biased at a different operating voltage, such that they have different responses to particular analytes based on the operating parameters.

Each gas sensor 108 is connected to a data processing apparatus 116 which is configured to collect data from the gas sensors 108, e.g., response data 118. Response data 118 can include a time-dependent response of each of the gas sensors 108 to a test gas. Additionally, the data processing apparatus 116 can be configured to collect time-dependent measurements of operating conditions of the plurality of sensors 108, gas inlet 110, environmental controller 124, and desorption controller 142, e.g., temperature and relative humidity, gas flow rate, gas pressure, and the like.

In some implementations, response data 118 includes a measure of the resistivity of the gas sensor 108 versus time. Further discussion of the response data is discussed with reference to FIGS. 3A-C below.

Data processing apparatus 116 can be hosted on a server or multiple servers in data communication with the gas sensors over a network. The network may include, for example, one or more of the Internet, Wide Area Networks (WANs), Local Area Networks (LANs), analog or digital wired and wireless telephone networks (e.g., a public switched telephone network (PSTN), Integrated Services Digital Network (ISDN), a cellular network, and Digital Subscriber Line (DSL)), radio, television, cable, satellite, or any other delivery or tunneling mechanism for carrying data. The network may include multiple networks or subnetworks, each of which may include, for example, a wired or wireless data pathway. The network may include a circuit-switched network, a packet-switched data network, or any other network able to carry electronic communications (e.g., data or voice communications). For example, the network may include networks based on the Internet protocol (IP), asynchronous transfer mode (ATM), the PSTN, packet-switched networks based on IP, X.25, or Frame Relay, or other comparable technologies and may support voice using, for example, VoIP, or other comparable protocols used for voice communications. The network may include one or more networks that include wireless data channels and wireless voice channels. The network 505 may be a wireless network, a broadband network, or a combination of networks including a wireless network and a broadband network.

Data processing apparatus 116 can be configured annotate the response data 118 received from the gas sensors 108 responsive to a test gas. In some implementations, annotation data 120 includes timestamps, e.g., a start time label, a stop time label, and/or respective composition data 122 of the test gases, e.g., a set of known analytes of interest and set of known analytes not of interest, being evaluated using the gas sensing apparatus 102. In some implementations, the composition data 122 includes concentrations of the analytes of interest, concentrations of the analytes not of interest, or concentrations of both.

In some implementations, the data processing apparatus 116 is configured to generate annotation data 120 before, during, and after exposure of a test gas to the gas sensors 108, where the annotation data 120 includes recording a first label describing a first state of the multi-modal gas sensing array, e.g., a start time of the gas exposure. The gas manifold 126 can provide a first test gas to the multi-modal array of gas sensors 108, where the first test gas includes a first concentration of a known analyte of interest and a second concentration of a known analyte that is not of interest, e.g., a confounding gas. The data processing apparatus 116 can then collect a set of sample data 118 from each of the gas sensors 108 of the multi-modal gas sensing array responsive to the first test gas and then record annotation data 120, e.g., a second label, describing a second state of the multi-modal gas sensing array, e.g., a stop time of gas exposure. Further details of processes for the gas sensing apparatus 102 are discussed with reference to FIGS. 7A-8 below.

In some implementations, the data processing apparatus 116 further generates, from the response data 118, the annotation data 120, and the composition data 122 for the known test gases, training data for a machine-learned model. Details described in further detail below with reference to FIG. 8.

In some implementations, the data processing apparatus 116 is in data communication with an environmental controller 124. The environmental controller 124 may be a part of the data processing apparatus 116. For example, environmental controller 124 can be implemented as a software routine executed by data processing apparatus 116. The environmental controller 124 can be configured to provide operating instructions to the environmental regulator 106, gas sensors 108, data processing apparatus 116, and gas manifold 126. In some implementations, the environmental controller 124 can be configured to receive operational feedback, e.g., solenoid valve status, temperature control, etc., from one or more of the environmental regulator 106, gas sensors 108, data processing apparatus 116, and gas manifold 126.

In some implementations, the environmental controller 124 can receive operating conditions feedback, e.g., temperature, humidity readings, from a temperature and/or humidity gauge 128. The gauge 128, e.g., a thermocouple, hygrometer, or the like, can be in physical contact with the housing 104 or gas sensors 108 to measure a temperature and/or relative humidity. The gauge 128 can additionally or alternatively measure a temperature and/or relative humidity of the gas present within the housing 104.

In some implementations, the operating conditions feedback received by the environmental controller 124 can be provided to the data processing apparatus 116 and recorded as annotation data 120. For example, temperature of the housing 104, gas sensors 108, and test gas can be recorded as annotation data 120 and included with the response data 118 for the particular test gas.

In some implementations, the data processing apparatus 116 is in data communication with a desorption controller 142. The desorption controller 142 may be a part of the data processing apparatus 116. For example, desorption controller 142 can be implemented as a software routine executed by data processing apparatus 116. The desorption controller 142 can be configured to provide operating instructions to sorbent tube pre-filter system 140 and data processing apparatus 116. The desorption controller 142 can control the sorbent tube pre-filter system 140 to separately desorb the content of sorbent tubes in the sorbent tube pre-filter system 140 and to pass the desorbed content to the gas sensors 108 for analysis. In some implementations, the desorption controller 142 can be configured to receive operational feedback, e.g., sorbent tube pre-filter status data, sorbent tube information, etc., from one or more of the sorbent tube pre-filter system 140 and data processing apparatus 116. Sorbent tube pre-filter status data can include, but is not limited to, operational status of sorbent tube pre-filter valves, heaters, pumps, fans, purge systems, or a combination thereof. Sorbent tube information can include, but is not limited to, data identifying a type of a sorbent tube (e.g., the analyte or set of analysts that a tube is sensitive to), a position of the tube within a sorbent tube array, a number of times that a sorbent tube has been activated (e.g., the number of times that content has been desorbed from the sorbent tube), or a combination thereof.

In some implementations, the operating conditions feedback received by the pressurization controller 142 can be provided to the data processing apparatus 116 and recorded as annotation data 120. For example, sorbent tube information associated with a sorbent tube from which a test gas sample was desorbed can be recorded as annotation data 120 and included with the response data 118 for the particular test gas.

The system 100 further includes a gas manifold 126 having multiple gas sources 130. The multiple gas sources 130 can each include multiple known analytes of interest and multiple known analytes not of interest. For example, gas manifold 126 can include gas source 130a, 130b each having analytes of interest and gas sources 130c and 130d each having analytes not of interest (e.g., confounding gases).

Gas manifold 126 can be a closed-loop system, where no external compounds are present within the gas manifold 126 that could interfere with the test gases provided by the gas manifold to the gas sensing apparatus 102 via the gas inlet 110. The test gases provided by the gas manifold 126 to the gas sensing apparatus 102 can be composed only of the known analytes of interest and known analytes not of interest from the one or more gas sources 130.

Gas manifold 126 can further include regulatory components 132 which can be operable to selectively allow a controlled flows (e.g., 0-5 cubic feet/hour) of one or more of the gas sources 130 from the gas manifold 126 and into the gas inlet 110 to generate a particular test gas for the gas sensing apparatus 102. Further details of the gas manifold 126 are discussed with reference to FIG. 2.

Figure 2:
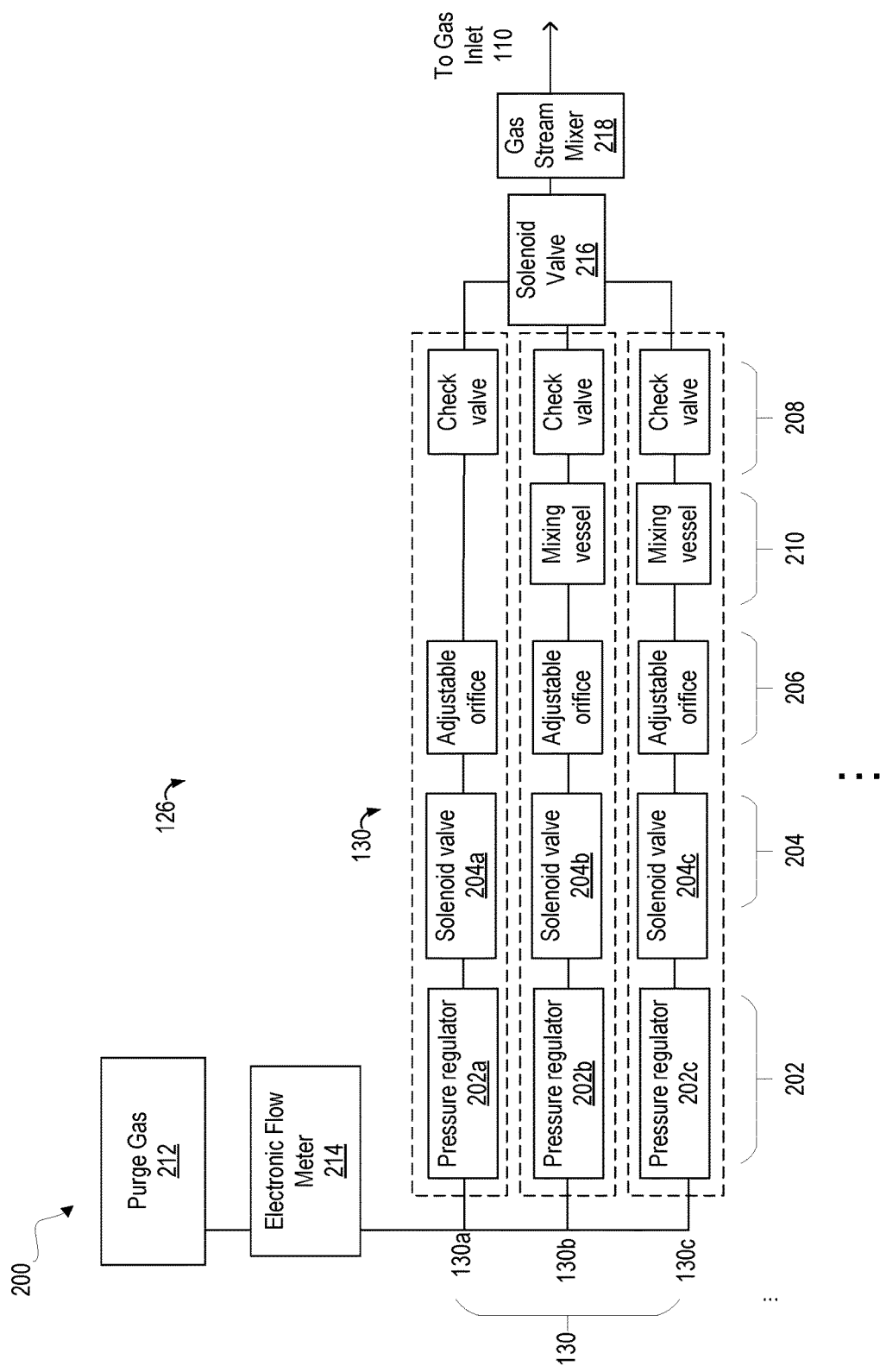
FIG. 2 is a block diagram of another example system for training the e-nose gas sensing apparatus.

FIG. 2 is a block diagram of another example system 200 for training the e-nose gas sensing apparatus 102. As described with reference to FIG. 1, the gas manifold 126 can include one or more regulatory components 132 for each gas source 130 that are configured to determine which of the gas sources 130 are selected to flow from the gas manifold 126 to the gas inlet 110 and further into the gas sensing apparatus 102. Referring now to FIG. 2, the system 200 depicts in further detail the gas manifold 126 that can be used to provide test gases to the e-nose gas sensing apparatus 102. Additional configurations of the gas manifold are possible, where a gas manifold 126 can include additional or fewer elements than those described with reference to FIG. 1 and FIG. 2.

As depicted in FIG. 2, each gas source 130 of the gas manifold 126 includes a pressure regulator 202, a solenoid valve 204, an adjustable orifice 206, and a check valve 208, which can be utilized in combination to control the flow of gas for each gas source 130. One or more of the components of each gas source 130 mentioned can be electronically controllable, e.g., an electronically adjustable orifice 206, by the environmental controller 124.

One or more of the gas sources 130, e.g., gas source 130b, can further include a mixing vessel 210. Mixing vessel 210 can be a vessel containing an item, e.g., coffee grounds, or a secondary gas source (e.g., a methane tank) that provides an analyte to the gas source 130.

Pressure regulator 202 can regulate a pressure from a purge gas source 212, e.g., a compressed gas cylinder, from a high pressure to a low pressure to generate a desired flow rate of the purge gas into the gas sources 130, e.g., into a mixing vessel 210. The purge gas source 212 can include a compressed air source, e.g., clean dry air, and/or an inert gas source, e.g., nitrogen, argon, or the like. The purge gas source 212 can be regulated by an electronic flow meter 214 which controls a flow rate of the purge gas source 212 into the various gas sources 130, where pressure regulator 202 for each gas source 130 can further regulate a flow of the purge gas into the particular gas source 130.

In some implementations, a gas source 130a is only composed of purge gas from gas source 212, e.g., compressed air and/or inert gas, which is provided to a gas inlet 110 without any analytes of interest or analytes not of interest present.

In some implementations, a gas source, e.g., gas source 130b, is a first gas source, where the first gas source is generated by mixing at least the purge gas source 212 with an analyte present in the mixing vessel 210b, e.g., coffee grounds, soil, methane, etc. A gas source, e.g., gas source 130b, can be a second gas source, where the second gas source is generated by mixing at least the purge gas source 212 with an analyte present in the mixing vessel 210c, e.g., ethanol, apples, charcoal, etc.

In some implementations, the gas manifold 126 further includes a solenoid valve 216 and a gas stream mixer 218. Solenoid valve 216 can be configured to control the flow of gases from the gas manifold 126 prior to entering the gas inlet 110. Solenoid valves 216 can receive operational instructions from the environmental controller 124 and/or from the data processing apparatus 116.

In some implementations, gas stream mixer 218 can be used to mix gases from multiple gas sources 130. For example, a first gas source 130b and a second gas source 130c can be allowed to flow to the gas stream mixer 218 and blended together to form a test gas that is provided to the gas inlet 110. Operation of the gas stream mixer 218 can be controlled by the environmental controller 124 and/or the data processing apparatus 116. Other methods for blending gases from multiple gas sources 130 prior to the test gas being provided to the gas inlet 110 are possible.

In some implementations, some or all of the pressure regulators 202, solenoid valves 204, adjustable orifices 206, mixing vessels 210, check valves 208, solenoid valve 216, electronic flow meter 214, and gas stream mixer 218 can be operated automatically and/or semi-automatically by the environmental controller 124. For example, the environmental controller 124 can be configured to provide process control instructions to the gas manifold 126 to provide, at the gas inlet 110, a particular test gas including a composition of analytes.

In some implementations, the environmental controller 124 can open and close solenoid valves 204 and 216 to determine which gas sources 130 flow into the gas inlet 110. The environmental controller 124 can control a flow rate for each pressure regulator 202 to establish a concentration of the particular analyte present in the mixing vessel 210 for the gas source 130. For example, mixing vessels 130b and 130c can include a same analyte (e.g., coffee grounds) and the environmental controller 124 can set pressure regulator 202b to a first flow rate and pressure regulator 202c to a second flow rate to achieve a gas source 130b with a first concentration of a given analyte and a gas source 130c with a second, different concentration of the given analyte.

Referring back to FIG. 1, for a particular test gas provided by the gas manifold through the gas inlet 110 of the e-nose gas sensing apparatus 102, response data 118 is collected from each of the gas sensors 108 of the gas sensing array. The gas sensors 108 can be a multi-modal array of gas sensors having a variety of response characteristics to a range of analytes. Different types of gas sensors 108 can be more or less responsive to a particular analyte, and a subset of the gas sensors 108 can be identified as optimally responsive to the particular analyte based in part on the response data 118 collected.

Figure 3A:
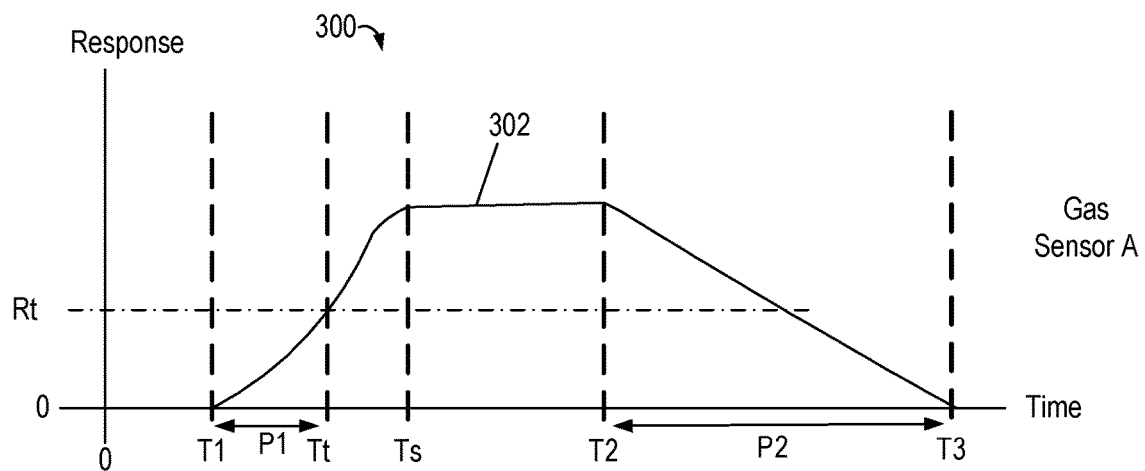
FIGS. 3A-3C are example plots of gas sensor responses for the e-nose gas sensing apparatus.
Figure 3B:
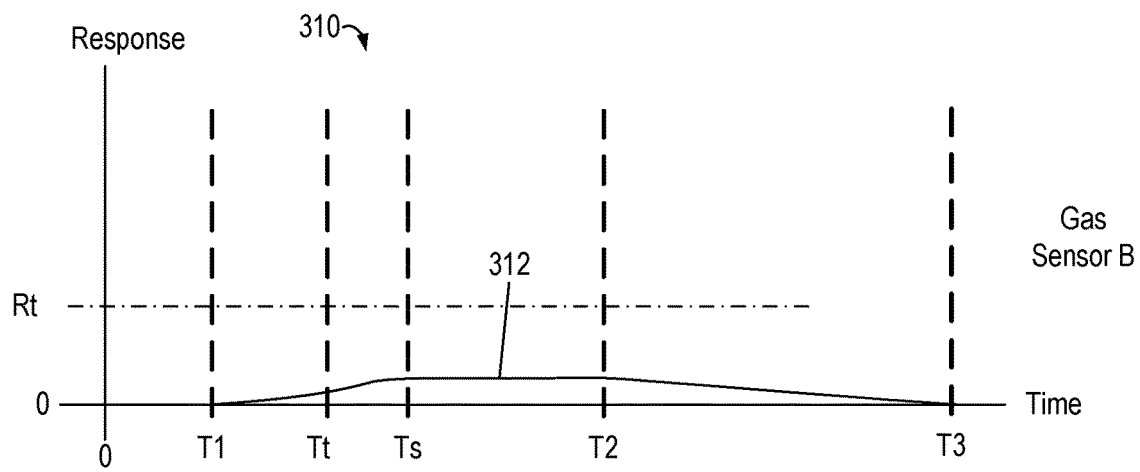
Figure 3C:
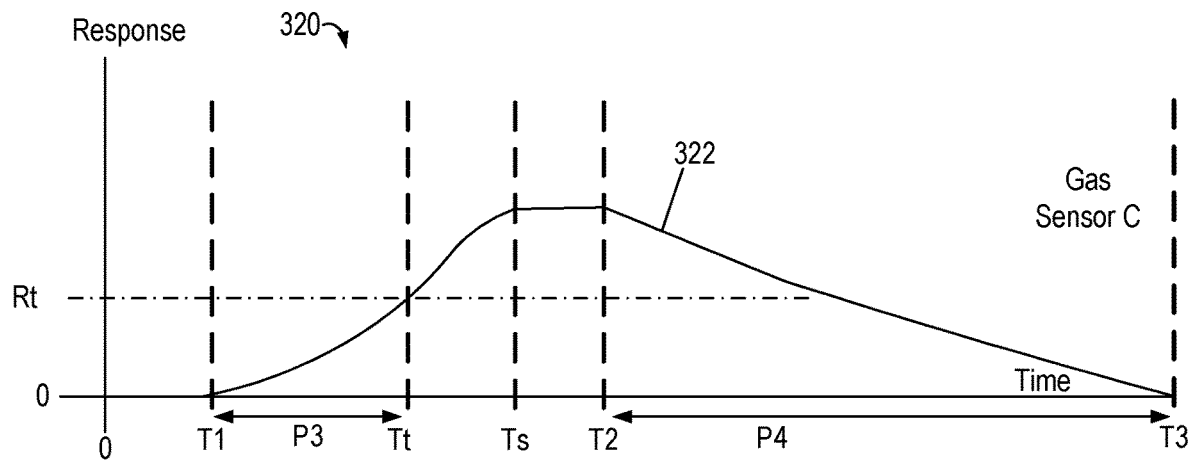

In some implementations, response of a gas sensor 108 to a test gas including one or more analytes can be measured as a change in gas sensor electrical resistivity before, during, and after exposure to the particular test gas (e.g., as in MOx sensors). In some implementations, response of a gas sensor 108 can be measured as an electrical signal generated by one or more analytes of interest that are present in the test gas (e.g., as in PID sensors). FIGS. 3A-3C are example plots of gas sensor responses for the e-nose gas sensing apparatus.

FIG. 3A depicts an example plot 300 of a response of a gas sensor A to a particular test gas including one or more analytes. Gas sensor A, e.g., gas sensor 108a, exhibits a response 302 to a particular test gas over time. The response 302 can be plotted versus time and annotation data, e.g., annotation data 120, can be recorded for the response 302. Annotation data 120 can include one or more timestamps, where T1 indicates a timestamp beginning the introduction of the test gas to the gas sensor A, T2 is a timestamp where the exposure to the test gas is terminated (e.g., the solenoid valve 216 is closed or the purge gas source 130a flows into the gas inlet 110), and T3 is a timestamp associated with the response of the gas sensor A reaching a baseline response Ro.

A baseline response Ro can be a response measurement for the gas sensor A prior to providing the first test gas, where T3 is the time stamp after termination of the gas exposure when the response 302 of the gas sensor A matches the baseline response measurement Ro. The baseline response measurement Ro can be a resistivity measurement for the gas sensor, where the resistivity of the gas sensor A is below a minimum threshold resistivity.

Additional timestamps can be recorded in the annotation data 120 for the plot 300, for example, a timestamp for threshold time Tt, when the response 302 of the gas sensor A reaches a threshold response Rt. In another example, a timestamp can be annotated when the response 302 of the gas sensor A reaches a saturation point Ts, in other words, when the response 302 of the gas sensor A saturates to the exposure of the test gas.

Threshold response Rt can be selected based in part on a concentration of the one or more analytes of interest in the test gas, e.g., for very low concentrations of analytes the threshold response Rt can be set lower than for relatively higher concentrations of analytes. Threshold response Rt can be selected based in part on the characteristics of the particular analytes in the test gas, e.g., a lower threshold response can be set for a highly dangerous and/or toxic analyte versus a higher threshold response can be set for a non-toxic analyte.

In some implementations, a threshold response Rt can depend in part on the one or more types of gas sensors of the multiple gas sensors 108 that are exposed to the test gas. For example, if all of the gas sensors have some amount of sensitivity to a particular analyte in the test gas, the threshold response may be set at a higher threshold response to select only the gas sensor(s) with a highest relative sensitivity to the particular analyte.

In some implementations, a threshold response Rt can depend in part on a type of gas sensor, for example, depending on a mechanism of detection for the type of gas sensor, in order to normalize the sensitivities of each type of gas sensor relative to each other type of gas sensors in the multi-modal array of gas sensors 108. A minimum response threshold can be defined as a lowest detectable limit of a particular analyte. For example, a threshold of detectability can be 1 part per million (ppm) for most MOx sensors when detecting acetone vapor.

As depicted in FIG. 3A, response 302 of the gas sensor A to the particular test gas reaches a threshold response Rt prior to the timestamp T2 where the gas sensor A exposure to the test gas is terminated, e.g., a solenoid 204b is closed and a solenoid 204a for the purge gas source 130a is opened. A second set of response data 118 can include a time-dependent recovery response P2 of the gas sensor A after terminating exposure at T2 of the gas sensor A to the test gas.

In some implementations, one or more of the gas sensors in the array of gas sensors 108, e.g., gas sensor 108b, do not meet a threshold response Rt to the particular test gas. FIG. 3B depicts an example plot 310 of a gas sensor B, e.g., gas sensor 108b, that has a response 312 to the particular test gas including the one or more analytes of interest over time. In contrast to the plot 300 depicted in FIG. 3A, the response 312 of the gas sensor B to the particular test gas does not reach the threshold response Rt prior to T2 where the gas sensor exposure to the test gas is terminated.

In some implementations, gas sensor B can have negligible response R to a test gas, where the response 312 of the gas sensor B is not measurable, e.g., below the sensitivity of the sensor. Gas sensor B can have zero response to a test gas, where the gas sensor 130 is nonreactive to analytes of interest in the test gas, e.g., an inorganic gas sensor 130 can have zero reactivity to an organic compound being tested.

In some implementations, multiple gas sensors 108 can have at least a threshold response Rt to a particular test gas, where a first gas sensor can have an optimized response to the particular test gas versus a second gas sensor. An optimized response can be defined as a shorter period of time between exposure to the test gas T1 and a time to reach a threshold response Rt. Referring to FIG. 3A, a period of time between the exposure to the test gas T1 and the time to reach the threshold response Tt is P1. A range of time for P1 can be, for example, 5-120 seconds.

In some implementations, an optimized response can be a period of recovery time for the gas sensor between the exposure of the gas being terminated T2 and the gas sensor reaching the baseline responsivity Ro, T3. Referring to FIG. 3A, a period of time between the timestamp when exposure of the gas is terminated T2 and the timestamp when the gas sensor reaches the baseline responsivity T3 is P2. A range of time for P2 can be, for example, 5-120 seconds.

Referring now to FIG. 3C, plot 320 depicts a response 322 of gas sensor C, e.g., gas sensor 108c, to the particular test gas. Gas sensor C has a period of time P3 between a timestamp marking the exposure to test gas T1 and a timestamp marking when the gas sensor C reaches the threshold response Rt at Tt. Gas sensor C also has a period of time P4 between the timestamp marking the exposure of the gas being terminated T2 and the timestamp marking when gas sensor C reaches the baseline responsivity Ro at T3. As depicted in FIGS. 3A and 3C, the period of time P3 for gas sensor C is greater than the period of time P1 for gas sensor A.

In some implementations, selecting a particular gas sensor with an optimized response is based on the particular gas sensor exhibiting a shorter period of time to reach a threshold response after exposure to the particular test gas and/or a shorter period of time to recover a baseline response Ro, e.g., selecting gas sensor A instead of gas sensor C because P1 is less than P3 and/or because P2 is less than P4.

In some implementations, each gas sensor having at least a threshold response Rt to the particular test gas can be compared to each other gas sensor having at least the threshold response to the particular test gas, and a particular gas sensor or set of two or more gas sensors of the multiple gas sensors can be selected based in part on the respective responses, e.g., response 302 and 322, of each gas sensor. The response data 118, e.g., including plots 300, 310, 320 of responses 302, 312, 322 respectively, for each gas sensor 108 of the multiple gas sensors can be analyzed and gas sensors having at least a threshold response Rt recorded in the set of response data 118 can be selected. A proper subset of gas sensors can include the gas sensors that have a difference between the third timestamp and first timestamp, e.g., between T3 and T1 that is less than a threshold time. A range of time for T3-T1 can be, for example, 5-120 seconds. Further discussion of the selection of the subset of gas sensors is discussed with reference to FIGS. 4 and 5.

E-Nose Multi-Modal Gas Sensing Apparatus

Figure 4:
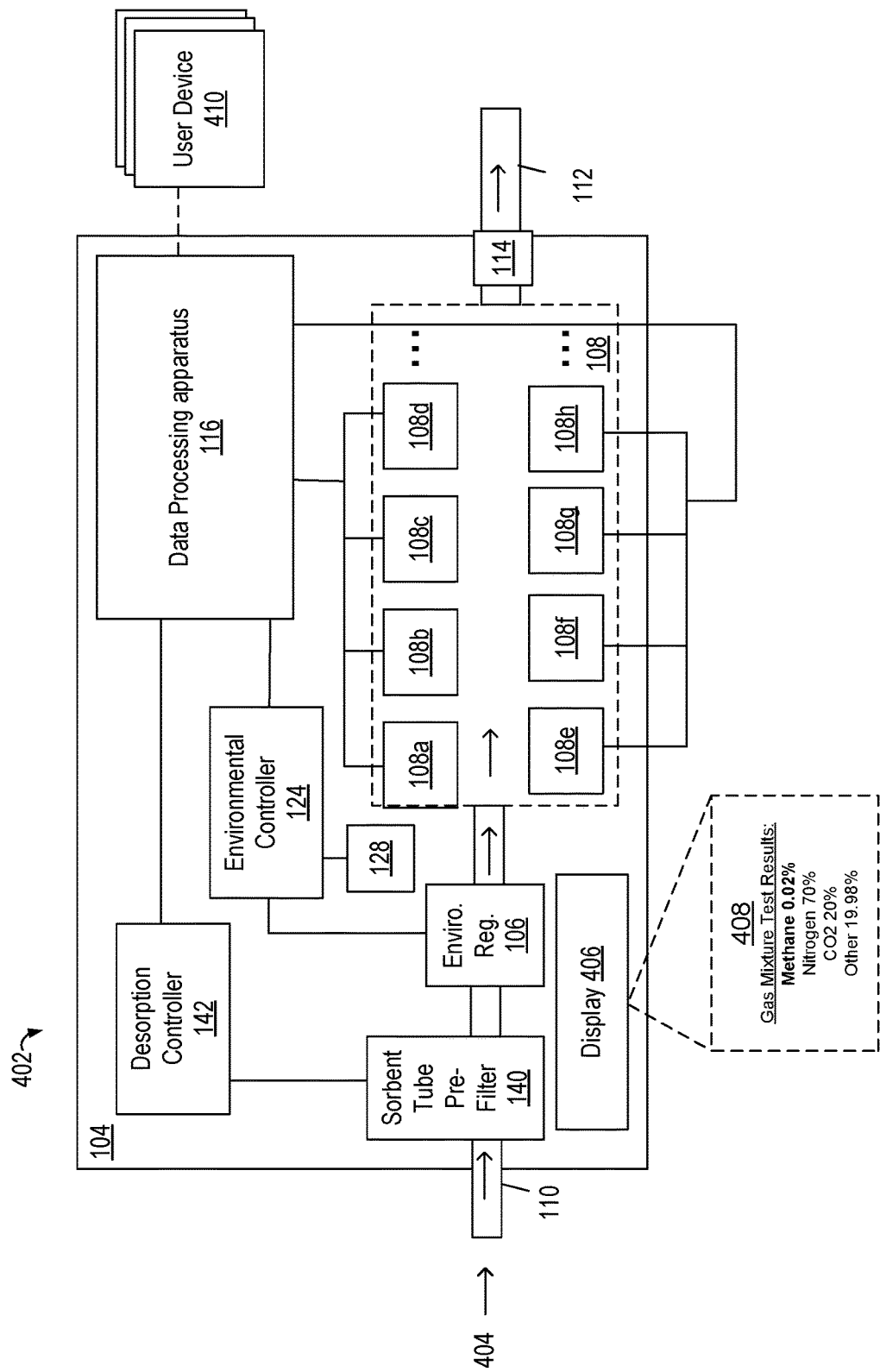
FIG. 4 is a block diagram of an example e-nose gas sensing apparatus.

FIG. 4 is a block diagram of an e-nose gas sensing apparatus 402. As discussed above with reference to FIG. 1, the e-nose gas sensing apparatus 402 includes a housing 104 including a gas inlet 110 configured to receive an unknown gas mixture 404 and a gas outlet 112 through which the unknown gas mixture 404 is purged from the e-nose gas sensing apparatus 402.

The gas inlet 110 is coupled to the housing 104 and configured to expose the multiple gas sensors 108 to an unknown gas mixture 404 that is introduced through the gas inlet 110. Unknown gas mixture 404 can be introduced passively via the environment surrounding the gas inlet 110. For example, the unknown gas mixture 404 can be introduced via the gas inlet 110 when the gas sensing apparatus 402 is deployed in a testing environment, e.g., in a factory setting, Passive introduction of the unknown gas mixture 404 into the gas inlet 110 can be, for example, by diffusion of the unknown gas mixture into the gas inlet 110.

In some implementations, the unknown gas mixture 404 can be introduced actively into the gas inlet 110, for example, by generating a negative pressure within the housing 104 using a fan 114 or other similar device. In another example, the unknown gas mixture 404 can be introduced actively to the gas inlet 110 by a positive pressure of the gas at the gas inlet, e.g., by a person blowing into the gas inlet 110, a gas exhaust from a piece of equipment, or the like.

Multiple gas sensors 108 including a first type of gas sensor, e.g., gas sensor 108a, and a second type of gas sensor, e.g., gas sensor 108b, that is different from the first type of gas sensor are located within the housing 104 where each of the first type of gas sensor and second type of gas sensor is sensitive to a respective set of analytes. The first type of gas sensor 108a and the second type of gas sensor 108b can have different methods for gas sensing, e.g., where the first type of sensor is a MOx sensor and the second type of sensor is a PID sensor.

In some implementations, the first type of gas sensor 108a and the second type of gas sensor 108b have a same method for gas sensing but are configured to have different performance parameters, e.g., a MOx sensor operating at a first operating temperature and a MOx sensor operating at a second operating temperature. Operating the MOx sensors at different temperatures can cause each respective MOx sensor to respond differently to analytes in a test gas, even when sensing a same test gas at a same concentration.

Gas sensing apparatus 402 further includes an environmental controller 124 coupled to the housing 104 and configured to regulate temperatures of the housing 104, gas inlet 110, and gas sensors 108 to a particular temperature. The environmental controller 124 can include an environmental regulator 106, for example, a heating source and heat-transfer fins, embedded into the housing 104 where gas introduced at the gas inlet 110 passes through heating channels within the heat-transfer fins of the housing 104 to stabilize a temperature of the gas 404 to the particular temperature. In some implementations, the environmental controller 124 can include temperature and/or humidity gauges 128 to measure a temperature and/or relative humidity of the unknown gas mixture 404 that is received at the gas inlet 110.

Gas sensing apparatus 402 includes a data processing apparatus 116 in data communication with the gas sensors 108 and the environmental controller 124. The data processing apparatus 116 can be an onboard computer that is affixed to the housing 104 of the apparatus 402. In some implementations, a portion or all of the data processing apparatus 116 can be hosted on a cloud-based server that is in data communication with the gas sensing apparatus 402 over a network.

Data processing apparatus 116 can include a user device 410, where a user can interact with the gas sensing apparatus 402 via the user device 410, e.g., receive data, provide testing instructions, receive testing information, or the like. User device 410 can include, for example, a mobile phone, tablet, computer, or another device including an application environment through which a user can interact with the gas sensing apparatus 402. In one example, user device 410 is a mobile phone including an application environment configured to display gas mixture test results for the unknown gas mixture 404, allow for user interaction with the gas sensing apparatus 402, and the like.

In some implementations, the apparatus 402 includes a display 406 configured to communicate information 408 to a user of the gas sensing apparatus 402 and/or allow for user interaction with the gas sensing apparatus 402. Information 408 can include, for example, the operational status of the apparatus 402, e.g., on/off, testing, processing, etc.

In some implementations, information 408 includes test results for the unknown gas mixture 404. Information 408 can be presented to a user based on user preferences, e.g., to highlight a particular set of analytes that the user is interested in discovering in the unknown gas mixture 404. Information 408 can be additionally or alternatively provided to one or more user devices 410 in data communication with the apparatus 402.

In some implementations, display 410 is configured to respond to user interaction, e.g., a touch-screen functionality. Display 410 can further include audio feedback, e.g., an alert, to notify a user of the status of the apparatus 402. For example, the apparatus 402 can provide an audio and/or visual update to the user of a testing status. In another example, the apparatus 402 can provide an audio and/or visual alarm to the user, e.g., if a particular analyte is detected above/below a preset threshold, e.g., a threshold concentration of the analyte is detected in the ambient.

In some implementations, imaging data can be captured of an environment surrounding the apparatus 402, e.g., using a camera or video recording device. The imaging data of the surrounding environment can be displayed on display 410 to identify, to a user, one or more objects in the surrounding environment that may be included in the unknown gas mixture 404 being sampled by the apparatus 402. A blend ratio of the various analytes that are being sensed in the unknown gas mixture 404 can be displayed on display 410.

Gas sensing apparatus 402 can also include a sorbent tube pre-filter system 140 and desorption controller 142. Sorbent tube pre-filter system 140 is configured to separate different analytes or sets of analytes from a gas into an array of different sorbent tubes, and separately desorb and pass the individual analytes (or sets of analytes), i.e., the content of each sorbent tube, to the gas sensors 108. In other words, the sorbent tube pre-filter system 140 forms an analyte selective pre-filter for the gas sensing apparatus that can serve to disambiguate output from gas sensor(s) 108 that might be responsive to multiple different analytes (e.g., as discussed above in reference to FIG. 1). In some implementations, the desorption controller 142 is configured to control the sorbent tube pre-filter system 140 in coordination with data processing apparatus 116 to obtain sensor response measurements of analytes contained in the gas 404. For example, desorption controller 142 can be configured to control the sorbent tube pre-filter system 140 to separately desorb the content of the sorbent tubes in the sorbent tube pre-filter system 140 and to pass the desorbed content to the gas sensors 108 for analysis (e.g., as discussed above in reference to FIG. 1). The sorbent tube pre-filter system 140 is discussed in more detail below with reference to FIGS. 5 and 6.

Further details of the gas sensing apparatus 402 are discussed with reference to FIGS. 10A-10D below.

Example Sorbent Tube Pre-Filter for a Multi-Modal Gas Sensing Apparatus

Figure 5:
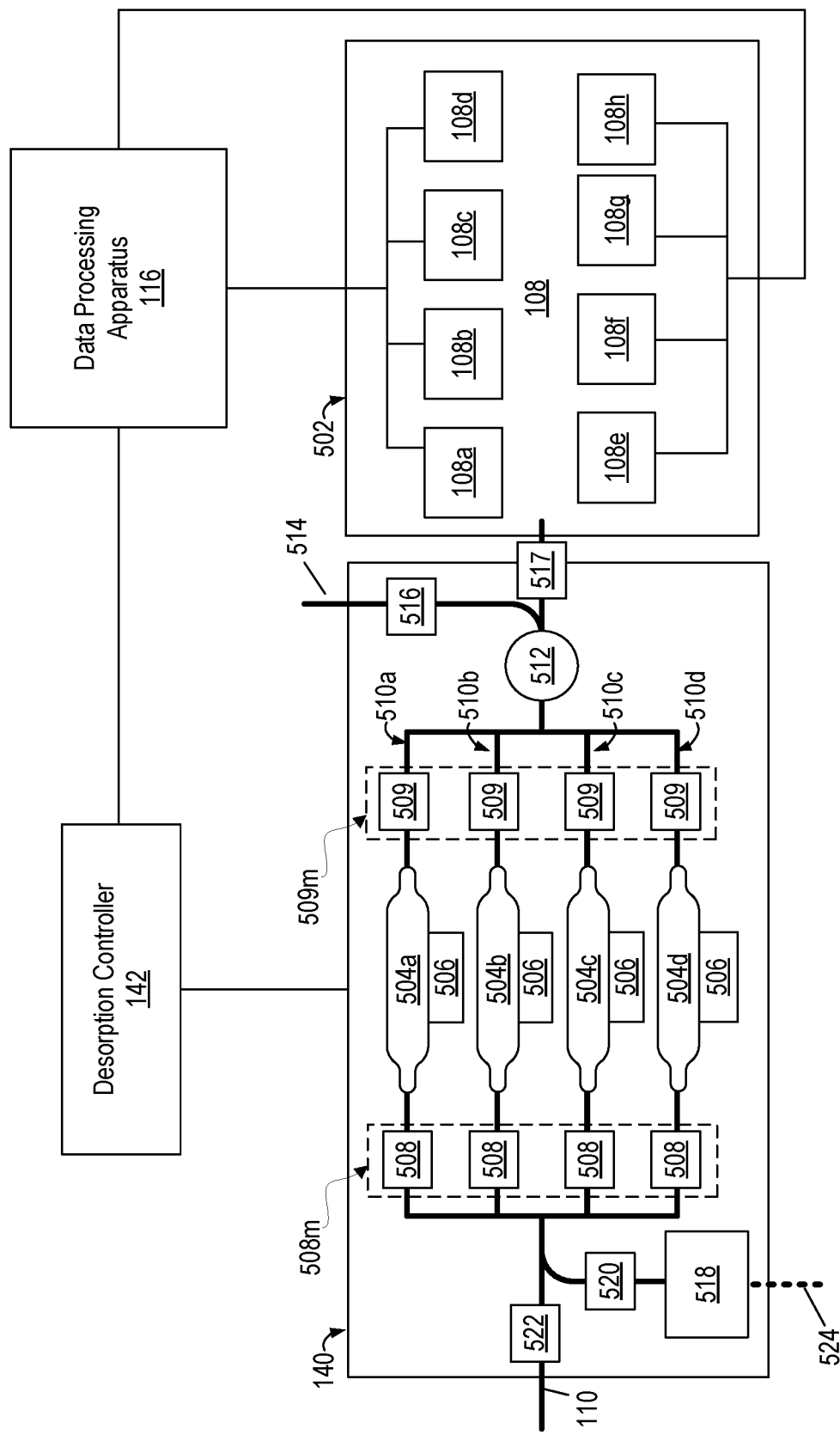
FIG. 5 is a block diagram of an example pre-filtering sorbent tube array for an e-nose gas sensing apparatus.

FIG. 5 is a block diagram of one example sorbent tube pre-filter system 140 for an e-nose gas sensing apparatus. Sorbent tube pre-filter system 140 includes an array of sorbent tubes 504a-504d (referred to collectively as sorbent tube array 504) and multiple flow paths 510a-510d providing fluidic communication between the sorbent tubes 504a-504d and a sensor chamber 502 in which the gas sensors 108 are disposed. Sorbent tubes 504a-504d can be sensitive to a different sets of gas analytes. That is, sorbent tubes 504a-504d in sorbent tube array 504 can be configured to adsorb different sets of gas analytes. For example, sorbent tube 504a can include an adsorbent material (i.e., a sorbent) that traps one particular gas analyte (or set of gas analytes) (e.g., methanol) and sorbent tube 504b can include a different sorbent material that traps a different gas analyte (or set of gas analytes) (e.g., ethanol). Although the sorbent tubes 504a-504d are illustrated as being connected in parallel flow paths, in some implementations, one or more sorbent tubes can be coupled in series along a common flow path. For instance, a second sorbent tube can be installed in series with sorbent tube 504a along flow path 510a.

The sorbent tube array 504 can include fixtures to hold the sorbent tubes 504a-504d in position within the array. In some implementations, the sorbent tubes 504a-504d are removable. For example, the fixtures can be configured to allow the sorbent tubes 504a-504d to be removed and replaced with different sorbent tubes. For example, the sorbent tubes 504a-504d can be replaced when the sorbent material becomes used up, e.g., less effective over time. As another example, the sorbent tubes 504a-504d can be swapped for sorbent tubes that are sensitive to different analytes, e.g., permitting users to reconfigure the sorbent tube array 504 to a particular use.

The sorbent tube pre-filter system 140 includes sorbent tube inlet and outlet isolation valves 508, 509. Isolation values 508, 509 can be controlled by desorption controller 142 to selectively isolate each sorbent tubes 504a-504d from its respective flow path 510a-510d. The isolation values 508, 509 can be implemented as individual valves or as value manifolds (represented by 508m and 509m).

A desorption device 506 is positioned proximate to each sorbent tube 504a-504d. Each desorption device 506 can be independently controlled by the desorption controller 142 to cause its associated sorbent tube to desorb, e.g., to release, analyte contents adsorbed by the sorbent material in the sorbent tube. Mechanisms for desorbing the content of a sorbent tube 504 can include, but are not limited to, heat, reductive/oxidative desorption, electron-stimulated desorption, or passing a carrier gas with higher affinity to a sorbent in the sorbent tube relative to the analyte. For example, desorption devices 506 can be, but are not limited to, heaters, electrodes configured to reverse an electrical bias on the sorbent tube (e.g., affecting reductive/oxidative desorption), an electron source configured to perform electron-stimulated desorption, or desorption carrier gas source.

The sorbent tube pre-filter system 140 can include a flow control device 512 such as a pump or fan. The flow control device 512 can be used for drawing gas through the sorbent tubes 504a-504d to collect analytes and/or to draw desorbed contents from a sorbent tube into the chamber 502 that contains the gas sensors 108. In some implementations, the sorbent tube pre-filter system 140 can use the gas sensing apparatus's 102 fan 114 (see FIGS. 1 and 4) as the flow control device 512.

In some implementations, the sorbent tube pre-filter system 140 can include an exhaust flow path 514 with an exhaust isolation valve 516 and a chamber isolation valve 517. The exhaust flow path 514 can be used when drawing test gas through the sorbent tube array 504 without exposing the gas sensors 108 to the test gas, e.g., by closing valve 517. For instance, in some implementations, it may be desirable to only expose the gas sensors 108 to the individually desorbed contents from the sorbent tube array 504. In some implementations, it may be useful to draw an initial test gas sample through the sorbent tube array 504 and then pass the filtered gas sample into the chamber (e.g., by isolating or not including exhaust flow path 514), e.g., to detect analytes that will not be adsorbed by the sorbent tube array 504.

In some implementations, the sorbent tube pre-filter system 140 can include flush gas source 518. The clean gas source 518 can be isolated by an isolation valve 520. The clean gas source can be configured to provide a clean gas for flushing the desorbed content of the sorbent tubes 504a-504d into the chamber 502 and/or for purging the chamber 502 between the desorption of content from different sorbent tubes. For purging the chamber 502 between the desorption of content from different sorbent tubes the clean gas source 518 can be passed to the chamber 502 through a flow path that bypasses the sorbent tube array 504 (e.g., a bypass path (not shown)). The clean gas source 518 can be a reserve volume air, e.g., clean dry air, and/or an inert gas, e.g., nitrogen, argon, or the like. In some implementations, the clean gas source 518 be a high purity filter coupled to a gas inlet 524. The gas inlet 110 can also include an isolation valve 522, e.g., to isolate the gas inlet 110 during operations when the clean gas is being applied to the sorbent tube array 504.

In some implementations, the sorbent tube pre-filter system 140 includes sensor(s) configured to read sorbent tube information from a sorbent tube. For example, the sorbent tubes can include machine readable information, e.g., a machine readable code applied to a label on the sorbent tube. The sensors can be configured to detect the machine readable code and send the data to the desorption controller or the data processing apparatus 116 to interpret the code/decode the information. The machine readable code can identify the sorbent tube type, e.g., the analyte(s) that the sorbent tube is sensitive to. Example machine readable codes can include, but are not limited to, bar codes, QR codes, and radio frequency identification codes (e.g., RFID tags). The machine readable code sensors can be positioned to detect the machine readable code applied to the sorbent tubes 504a-504d when the tubes are installed within the sorbent tube array 504. In some implementations, the sorbent tube information, e.g., sorbent tube type or analytes that the sorbent tube is sensitive to, can be received from user input. For example, the data processing apparatus 116 can provide a user interface, through which the user can provide input identifying which types of sorbent tubes are installed in various locations of the sorbent tube array 504.

Chamber 502 can be composed of various materials that are selected to be non-reactive to a set of analytes to which the chamber 502 will be exposed. Materials for the chamber 502 can include, for example, Teflon, Teflon-coated aluminum or stainless steel, Delrin, or other materials that are resistant to the set of analytes.

Chamber 502 can include fixtures to hold an array of gas sensors 108 within the chamber 502. The fixtures can be configured to accommodate particular dimensions of the gas sensors, and a layout of the fixtures within the chamber 502 can be configured to designate particular locations for different types of gas sensors 108 within the chamber 502.

Figure 6:
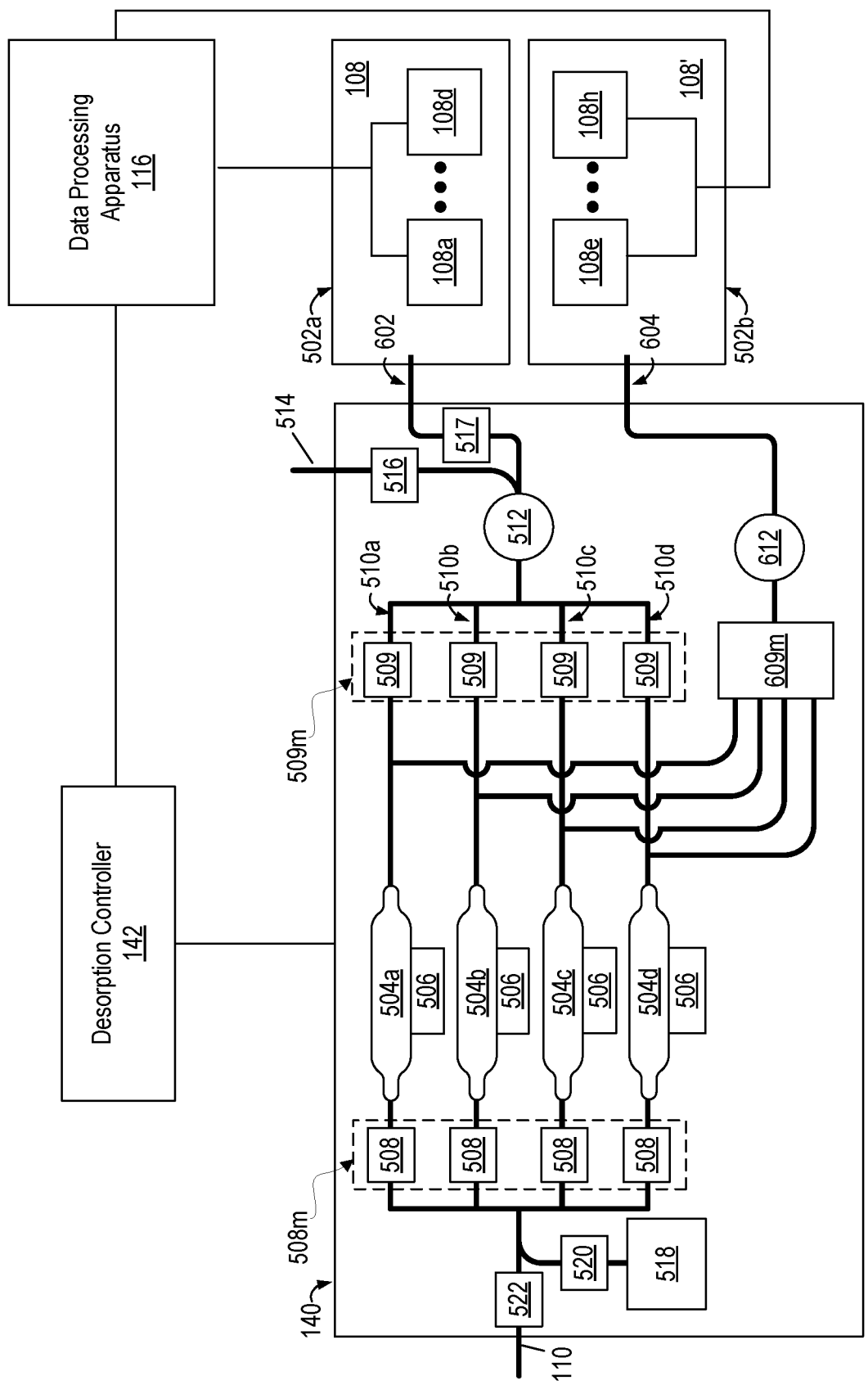
FIG. 6 is a block diagram of another example pre-filtering sorbent tube array for an e-nose gas sensing apparatus.

FIG. 6 is a block diagram of another example sorbent tube pre-filter system 140 for an e-nose gas sensing apparatus. The sorbent tube pre-filter system 140 depicted in FIG. 6 is similar to that depicted in FIG. 5, but includes multiple flow paths 602, 604 for desorbing the content of sorbent tubes of the sorbent tube array 504 into separate chambers 502a, 502b. For example, the gas sensing apparatus 102 can include multiple gas sensor chambers 502a, 502b, each containing a separate group of gas sensors 108, 108'. In such implementations, the sorbent tube pre-filter 140 can include additional flow paths 602, 604 to transfer desorbed contents from the sorbent tube array 504 to any of the chambers 502a or 502b. Each flow path 602 and 604 is directed to a different one of the chambers 502a, 502b and can include a separate set of isolation valves 509m and 609m and a separate flow control device 512, 612.

The operations of the sorbent tube pre-filter system 140 depicted in FIG. 6 are similar to that depicted in FIG. 5, with the additional ability to selectively direct desorbed content from the sorbent tube array 504 to any of the different gas sensor chambers 502a, 502b. For example, gas sensor array 108 can contain gas sensors that respond to different analytes than the gas sensors in gas sensor array 108'. In operation, the gas sensing device 102 (e.g., as controlled by data processing apparatus 116) can direct the desorption controller to desorb and transfer content from sorbent tube 504a to the gas sensors 108 in chamber 502a and to desorb and transfer content from sorbent tube 504b to the gas sensors 108' in chamber 502b. The data processing apparatus 116 can direct the desorption into appropriate chambers 502a, 502b based on sorbent tube type. For instance, the data processing apparatus 116 can select to desorb and transfer the content of sorbent tube 504a into the chamber 502a containing gas sensors 108 because the sensors 108 are more responsive to the type of analytes adsorbed by sorbent tube 504a than gas sensors 108'.

Example Operation of E-Nose Multi-Modal Gas Sensing Apparatus

The e-nose multi-modal gas sensing apparatus can operate in various modes, including a configuration mode, e.g., determining a subset of gas sensors to include in the gas sensing apparatus for a particular environment including a set of analytes of interest, a training mode, e.g., training a machine-learned model to identify various analytes of interest, and detection mode, e.g., where the e-nose multi-modal gas sensing apparatus is deployed in a testing environment.

Figure 7A:
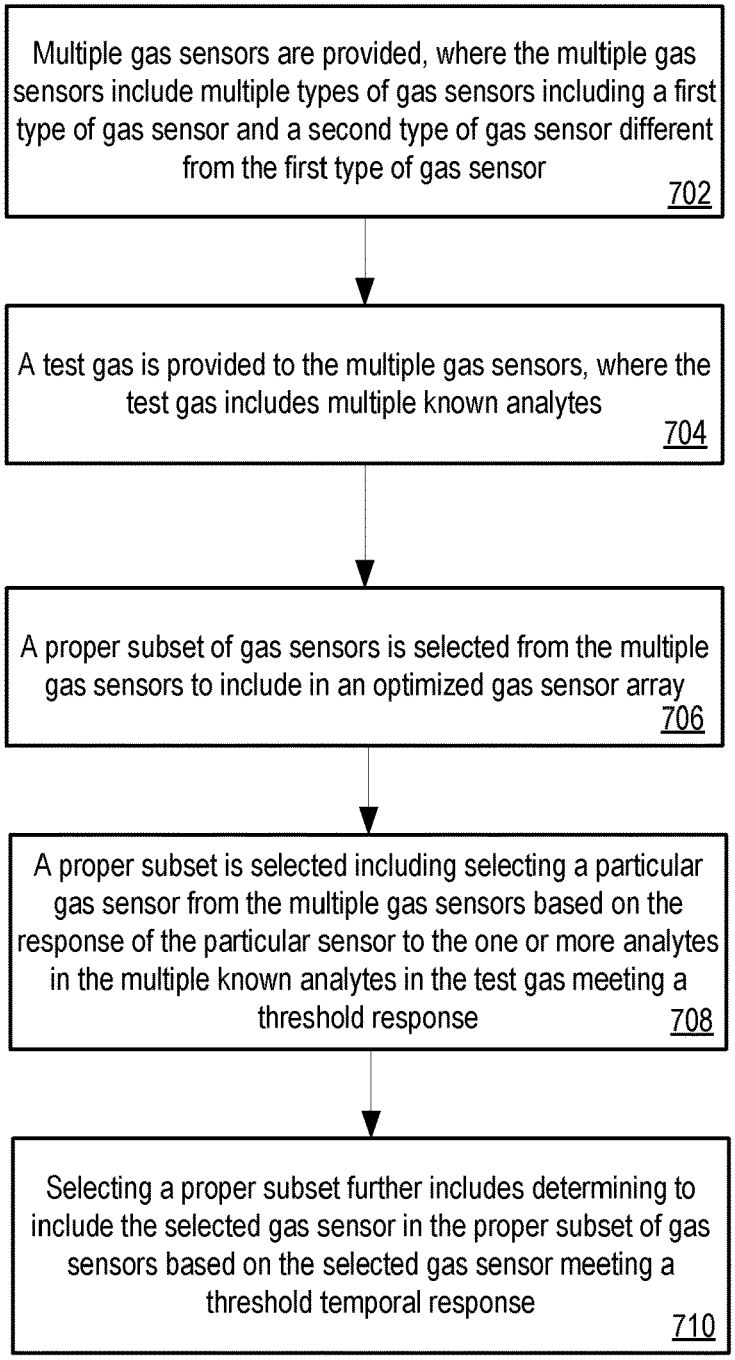
FIGS. 7A-8 are a flow diagrams of example processes of the e-nose gas sensing apparatus.

FIG. 7A is a flow diagram of an example process 700 of the e-nose gas sensing apparatus. E-nose gas sensing apparatus, e.g., gas sensing apparatus 102, can be configured to detect a particular set of analytes of interest utilizing process 700, where configuring the apparatus 102 can include determining a subset of gas sensors of a set of multiple gas sensors 108 from which to gather response data, e.g., response data 118.

In a first step, multiple gas sensors are provided, where the multiple gas sensors include multiple types of gas sensors, e.g., a first type of gas sensor and a second type of gas sensor different from the first type of gas sensor (702). As depicted in FIG. 1, multiple gas sensors 108 including a first type of gas sensor 108a and a second type of gas sensor 108b can be different types of sensors. For example, gas sensor 108a can be a MOx sensor and gas sensor 108b can be an electrochemical gas sensor. In another example, gas sensor 108a can be a MOx sensor operated at a first voltage bias and gas sensor 108b can be a MOx sensor operated at a second, different voltage bias.

In some implementations, the first type of gas sensor can be an organic-type gas sensor and the second type of gas sensor can be an inorganic-type gas sensor. For example, a volatile organic compound (VOC) sensor is sensitive to organic compounds, e.g., hydrogen, carbon dioxide, etc. In another example, PID sensors are sensitive to inorganic compounds, e.g., chlorine, tin oxide, etc.

A test gas is provided to the multiple gas sensors, where the test gas includes multiple known analytes (704). The test gas can be produced using a gas manifold, e.g., gas manifold 126, including multiple gas sources, e.g., gas sources 130. Each of the multiple gas sources 130 can include a different analyte, where the analytes can be mixed together using gas manifold 126 to generate a particular composition of known analytes in the test gas. The test gas can include a first concentration of a known analyte of interest and a second concentration of a known analyte not of interest. For example, 0.01% of methane and 0.99% of nitrogen or air.

The analytes of interest can be selected based on an intended environment for the apparatus with the selected set of gas sensors. For example, an industrial setting may have an interest in solvent analytes or processing gases. In another example, in an agricultural setting, analytes of interest are methane, pesticide compounds, or other agricultural by-products. In yet another example, in a laboratory setting, an analyte of interest can be a toxic or hazardous gas, e.g., chlorine gas. The analytes not of interest, or "confounding" gases can be selected to be inert gases, e.g., nitrogen, or as gases that are typically present in the intended environment for the apparatus with the selected set of gas sensors. For example, in a laboratory environment, an analyte not of interest can be nitrogen, solvent, e.g., isopropyl alcohol, or carbon dioxide. In another example, in an agricultural setting, analytes not of interest can be carbon dioxide, equipment exhaust, e.g., vehicle exhaust, or gasoline.

In some implementations, providing the test gas of known analytes to the multiple gas sensors 108 includes providing the test gas in a controlled environment including a particular temperature and a particular relative humidity. An environmental regulator, e.g., environmental regulator 106 including heat transfer fins, can be used to alter a temperature and/or relative humidity of the test gas prior to the test gas reaching the multiple gas sensors 108. Temperature and humidity of the test gas can be regulated, for example, to room temperature and a relative humidity below dew point.

In some implementations, the test gas is a sample of gas from a surrounding environment with unknown analyte concentrations.

In some implementations, providing the test gas to the gas sensors 108 includes providing the test gas at a flow rate of less than 5 cubic feet per hour for a known period of time. A flow rate can be, for example, as low as 1 cubic centimeter per minute. In another example, a flow rate can be up to 2 liters per minute. A particular flow rate can be selected based in part on a desired temperature and/or relative humidity of sampling and a temperature and/or relative humidity of the test gas prior to entering the gas inlet 110. In other words, an amount of time required to regulate the temperature and/or relative humidity of the test gas prior to exposure to the gas sensors 108 by the environmental regulator 106, e.g., heating fins, can determine a flow rate of the test gas within the environmental regulator 106.

Figure 7B:
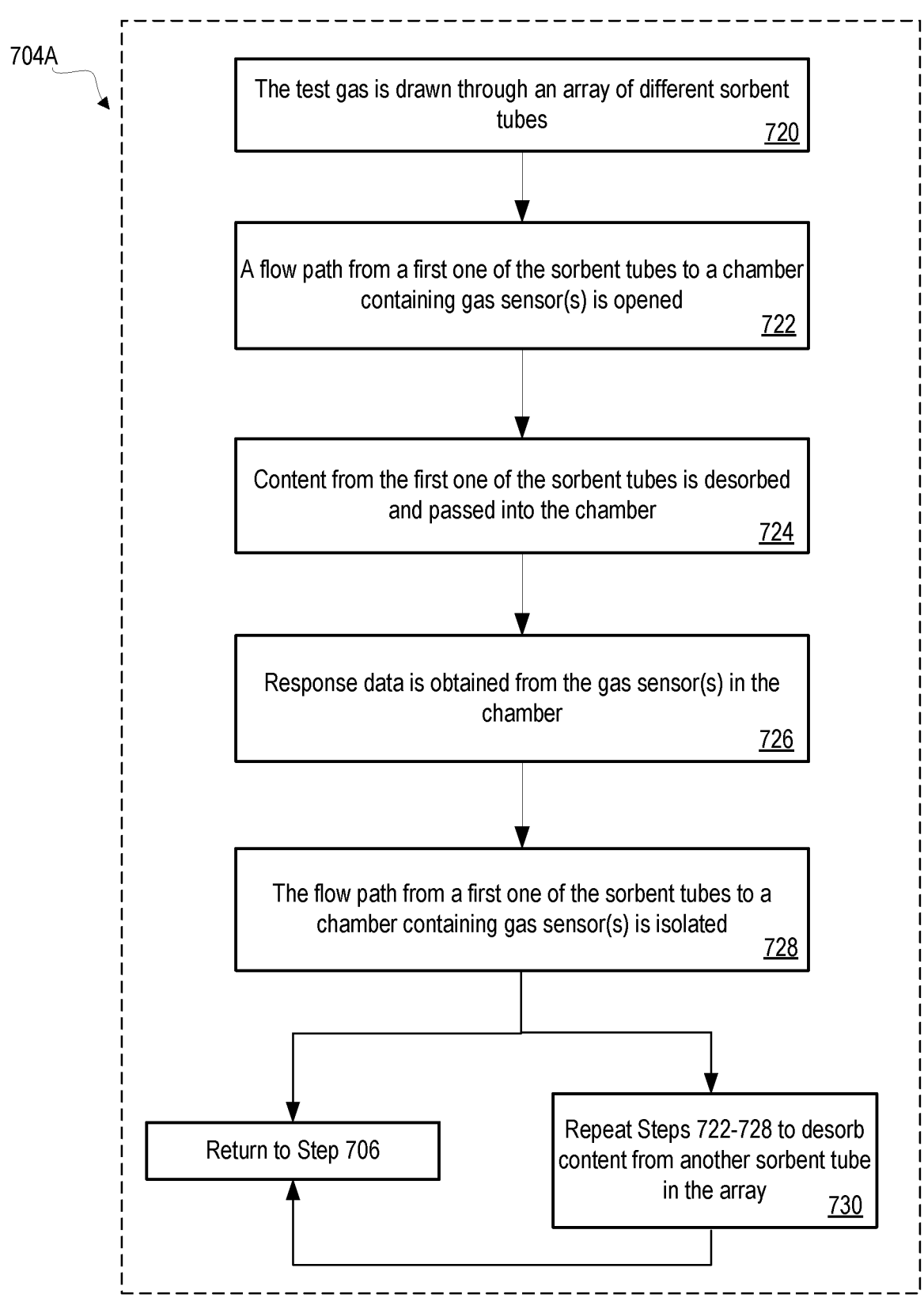

In some implementations, providing the test gas to the gas sensors 108 includes providing the test gas through a sorbent tube pre-filter system 140. FIG. 7B is a flow diagram of an example process 704A of the e-nose gas sensing apparatus for controlling operations of a sorbent tube pre-filter system 140. For example, process 704A can be performed by desorption controller 142 of FIGS. 1 and 4-6. In some implementations, process 704A can be directed by data processing apparatus 116, e.g., data processing apparatus can provide desorption controller 142 with instructions that coordinate desorption of content from individual sorbent tubes. For example, data processing apparatus can provide desorption controller 142 with instructions indicating which sorbent tube content to desorb into which sensor chamber or an order for desorbing content from the sorbent tubes. Process 704A is described with periodic reference to elements of the sorbent tube pre-filter systems 140 depicted in FIGS. 5 and 6.

The test gas is drawn through an array of different sorbent tubes (720). For example, a desorption controller can control isolation valves and a flow control device in the sorbent tube pre-filter system to direct the test gas through an array of sorbent tubes. For example, the desorption controller can open appropriate isolation valves to provide a flow path from an inlet of the sorbent tube pre-filter system (e.g., an inlet of the gas sensing apparatus 102) through an array of sorbent tubes. The desorption controller can control the operation of the flow control device (e.g., pump or fan) to obtain a desired flow rate of the test gas through the sorbent tube array. For example, the desorption controller can open inlet valve 522, open all of the sorbent tube inlet and outlet isolation valves 508, 509, and turn on flow control device 512.

In some implementations, the desorption controller can direct the test gas through a subset of sorbent tubes in the array that includes fewer than all of the sorbent tubes in the array. For example, the desorption controller can open only the isolation valves 508, 509 associated with the sorbent tubes that are to be used for analysis of a particular test gas. Or, in some circumstances, sorbent tubes may be missing from the array, e.g., the entire array may not be filled with sorbent tubes if some are being replaced or the sorbent tube array has the capacity to accept more sorbent tubes than are needed for a particular analysis. In such situations, empty sorbent tube fixtures may remain isolated.

In some implementations, the desorption controller directs the test gas out an exhaust outlet after passing through the sorbent tube array. For example, the desorption controller can close chamber isolation valve 517 and open exhaust isolation valve 516. In some implementations, the desorption controller directs the test gas into a chamber containing the gas sensors after passing through the sorbent tube array. In such implementations, the process 704A would proceed to Step 726 below to obtain response data from the gas sensors to the sorbent tube filtered test gas.

Once a desired volume of the test gas has been passed through the sorbent tube array, the desorption controller can isolate the sorbent tubes, e.g., by closing the respective isolation valves 508, 509 associated with each sorbent tube and turning off the flow control device 512.

A flow path from a first one of the sorbent tubes to a chamber containing gas sensor(s) is opened (722). The desorption controller establishes a flow path from a selected one of the sorbent tubes to a chamber containing the gas sensors. For example, the desorption controller opens appropriate isolation valves to established a flow path between the selected sorbent tube and the chamber. For instance, if sorbent tube 504a is the selected sorbent tube, the desorption controller can open its inlet and outlet isolation valves 508, 509 and open (if needed) the chamber isolation valve 517. In implementations in which the gas sensing apparatus 102 contains multiple gas sensor chambers, a flow path is established between the outlet of the selected sorbent tube and the appropriate chamber. For example, if the selected chamber is chamber 502a in FIG. 6, sorbent tube 504a's outlet isolation valve in valve manifold 509m would be opened. If the selected chamber is chamber 502b in FIG. 6, sorbent tube 504a's outlet isolation valve in valve manifold 609m would be opened.

In some implementations, the desorption controller obtains sorbent tube information from sensors in the sorbent tube array and passes the sorbent tube information to the data processing apparatus. Sorbent tube information can include, but is not limited to, data identifying a type of a sorbent tube (e.g., the analyte or set of analytes that a tube is sensitive to), a position of the tube within a sorbent tube array, a number of times that a sorbent tube has been activated (e.g., the number of times that content has been desorbed from the sorbent tube), or a combination thereof. The data processing apparatus can use the sorbent tube information to select which sorbent tube to align with which gas sensor chamber and pass appropriate instructions to the desorption controller.

Content from the first one of the sorbent tubes is desorbed and passed into the chamber (724). The desorption controller activates the desorption device associated with the selected sorbent tube to initiate desorption of any analytes adsorbed by the selected sorbent tube from the test gas. For example, the desorption controller activate a desorption mechanism of the desorption device 506 that is associated with sorbent tube 504a, e.g., the desorption device can turn a heater proximate to sorbent tube 504a to desorb analytes from sorbent material within the sorbent tube. The desorption controller can also control the operation of the flow control device 512 to pass the desorbed content (e.g., desorbed analytes from the test gas) along the established flow path and into the chamber containing the gas sensors. In some implementations, the desorption controller can control the operation of the flow control device to obtain a desired flow rate of the desorbed analytes into the chamber.

The desorption controller can open a flow path between the inlet of the selected sorbent tube and clean gas source (e.g., clean gas source 518 of FIGS. 5 and 6) in which to entrain and transport the desorbed analytes into the chamber. For example, the desorption controller can close an inlet isolation valve of the sorbent tube pre-filter system (e.g., valve 522) and open an isolation valve to the clean gas source (e.g., valve 520).

In some implementations, the desorbed analytes from the selected sorbent tube can be passed through the environmental regulator, e.g., environmental regulator 106, prior to being passed into the chamber. For example, the can be used to alter a temperature and/or relative humidity of the desorbed analytes prior to the desorbed analytes reaching the multiple gas sensors 108. Temperature and humidity of the desorbed analytes can be regulated, for example, to room temperature and a relative humidity below dew point.

Response data is obtained from the gas sensor(s) in the chamber (726). For example, data processing apparatus collects data generated by each gas sensor of the multiple gas sensors in response to the desorbed content of the sorbent tube, where the generated data from each gas sensor of the multiple gas sensors includes a response of the gas sensor to one or more analytes of the multiple known analytes in the desorbed content of the sorbent tube. Data processing apparatus 116 can collect response data 118, annotation data 120, and composition data 122 for each gas sensor 108 in response to desorbed content of the sorbent tube.

In some implementations, response data includes a response of the gas sensor 108 over a period of time. In one example, response data includes a measure of a change in electrical resistivity of the gas sensor over time. Each of a first type of gas sensor and the second type of gas sensor can have a different response to the multiple known analytes of desorbed content of the sorbent tube. For example, an organic-type gas sensor may react to an organic analyte, e.g., methane, in the test gas and not react to an inorganic analyte, e.g., tin oxide, in the test gas, and an inorganic-type gas sensor may not react to the organic analyte in the test gas and react to the inorganic analyte in the test gas.

As described above with reference to FIGS. 3A-3C, a gas sensor can have no response or a response below a threshold response to a particular analyte. A gas sensor can have a threshold response to a particular analytes. In some implementations, a change in electrical resistivity of a gas sensor 108 is measured prior to exposure to the test gas, e.g., timestamp T1, during exposure to the test gas, e.g., timestamp Tt, and after termination of exposure to the test gas, e.g., timestamp T2. A plot of the response of the gas sensor versus time of collection can be recorded for each gas sensor by the data processing apparatus, e.g., plots 300, 310, 320 as depicted in FIGS. 3A, 3B, and 3C, respectively.

In some implementations, the data processing apparatus can identify a particular analyte contained in the test gas based on the sorbent tube information associated with the selected sorbent tube and a sensor response from at least one of the gas sensors. For example, the data processing apparatus can distinguish analytes based on a gas sensor response and information indicating the set of analytes that a selected sorbent tube is sensitive to. In one example, if a particular gas sensor that is responsive to methanol generates a positive sensor response (e.g., a response equal to or above the sensor's threshold response Rt) when the content of a sorbent tube that adsorbs methanol is desorbed and passed to the gas sensors for analysis, the data processing apparatus can determine the test gas includes methanol.

The flow path from a first one of the sorbent tubes to a chamber containing gas sensor(s) is isolated (728). The desorption controller can isolate the selected sorbent tube and turn off the flow control device. For example, after a predetermined time has elapsed to ensure that a sufficient amount of the adsorbed analytes of the selected sorbent tube have been desorbed, the desorption controller can turn off the flow control device 512 and isolate the selected sorbent tube, e.g., by shutting its associated inlet and outlet isolation valves 508 and 509.

Steps 722-728 can be repeated to desorb content from another sorbent tube in the sorbent tube array and pass the desorbed analytes into the gas sensor chamber for analysis (730). In some implementations, the desorption controller can purge the gas sensor chamber prior to desorbing and providing the content from another sorbent tube into the gas sensor chamber. For example, the desorption controller can direct clean gas from the clean gas source 518 directly into the gas sensor chamber through a bypass path to purge the chamber.

Once the content of each sorbent tube in the sorbent tube array 504 (for which analysis is desired) has been desorbed and analyzed by the gas sensors, the process returns to step 706 of FIG. 7A.

Referring back to FIG. 7A, a proper subset of gas sensors is selected from the multiple gas sensors to include in an optimized gas sensor array (706). The proper subset of gas sensors 108 can include fewer than the full set of gas sensors. For example, a full set of gas sensors can include gas sensors 108a-108h, as depicted in FIG. 1, while the proper subset can include 108a, 108c, 108d, and 108h.

In some implementations, the proper subset of gas sensors 108 can include sensors that are responsive to at least one of the multiple analytes of the test gas. Each of the gas sensors of the proper subset of gas sensors 108 can be responsive to one or more of the multiple analytes of the test gas. For example, gas sensor 108a can be responsive to a first analyte, gas sensor 108c can be responsive to the first analyte and a second analyte, gas sensors 108d and 108h can both be responsive to the second analyte and a third analyte.

In some implementations, the proper subset of gas sensors 108 can include sensors that are unresponsive to one or more of the multiple analytes of the test gas. Sensors that are unresponsive may have zero response to a particular analyte or can have a response to an analyte below a threshold responsivity, e.g., Rt as discussed with reference to FIG. 3B. One or more of the gas sensors of the proper subset of gas sensors 108 can be unresponsive to one or more of the multiple analytes of the test gas. Continuing the example from above, gas sensor 108a can be unresponsive to the second and third analyte, gas sensor 108c can be unresponsive to the third analyte, and gas sensors 108d and 108h are unresponsive to the first analyte.

A proper subset is selected including selecting a particular gas sensor from the multiple gas sensors based on the response of the particular sensor to the one or more analytes in the multiple known analytes in the test gas meeting a threshold response (708). As described with reference to FIGS. 3A-3C, a gas sensor can have at least a threshold response Rt to one or more of the multiple analytes in the test gas. For example, gas sensor A and gas sensor C, as depicted in FIGS. 3A and 3C, respectively, both exhibit at least a threshold response to one or more of the analytes of the multiple analytes of the test gas. The proper subset can be selected to include the gas sensors that each meet a threshold response to one or more analytes of the multiple analytes of the test gas.

In some implementations, the subset of gas sensors that each meet the threshold response can include meeting a threshold reactivity to one or more analytes of the multiple analytes in the test gas. In one example, the threshold reactivity includes a threshold change in resistivity of the gas sensor in response to the one or more analytes, e.g., for a MOx sensor. In another example, the threshold reactivity includes a threshold oxidation or reduction of the one or more analytes at an electrode of the sensor, e.g., for an electrochemical sensor.

In some implementations, the threshold reactivity can be defined by a change of at least 0.1% relative to a total response range of a particular gas sensor. The threshold reactivity can be defined in part by what is considered a standard detectable signal for the particular gas sensor and can be different depending on the total response range of the particular gas sensor, e.g., can be different between a MOx sensor and an electrochemical sensor.

Selecting a proper subset further includes determining to include the selected gas sensor in the proper subset of gas sensors based on the selected gas sensor meeting a threshold temporal response (710). A threshold temporal response can include an amount of time between exposure of a particular gas sensor to the test gas and the particular gas sensor reaching the threshold response Rt. In one example, as depicted in FIGS. 3A and 3C, each of the gas sensor A and gas sensor C has a different amount of time, P1 and P3, respectively, to reach the threshold response Rt. A threshold temporal response can be greater than P1 but less than P3, such that gas sensor A is selected to be included in the proper subset but gas sensor C is not selected to be included in the proper subset as result.

As depicted in FIGS. 3A-C, the threshold temporal response can further include an amount of recovery time for the particular gas sensor to reach a baseline reading after termination of exposure to the test gas. In other words, an amount of time it takes for the gas sensor to recover from exposure to the test gas before it can be exposed again to another test gas.

In some implementations, a first gas sensor and a second gas sensor can be selected for inclusion in the proper subset of gas sensors based on the respective responses of the gas sensors, where the first gas sensor and the second gas sensor are determined to have similar responses to a same set of analytes of the plurality of analytes, e.g., both meet a threshold response Rt within a period P1. A first temporal response of the first gas sensor can be determined to be less than a second temporal response of the second gas sensors, where only the first gas sensor is then determined to be utilized in the subset of gas sensors. In one example, as depicted in FIGS. 3A and 3C, each of the gas sensor A and gas sensor C has a different amount of recovery time, P2 and P4, respectively, to reach the baseline response at timestamp T3. The threshold temporal response can be less than P4 but greater than P2, such that gas sensor A is selected to be included in the proper subset but gas sensor C is not selected to be included in the proper subset as result. In one example, if a gas sensor of the array of gas sensors 108 does not respond to an analyte of interest or does not have a response that is at least 0.1% of its total response range, the gas sensor can be excluded from the proper subset.

In some implementations, a threshold temporal response and threshold response for selecting the proper set of sensors depends in part on the subset of sensors of the multiple sensors that have non-zero responsivity to the test gas. For a test gas with a very low concentration of analytes of interest and/or analytes that are relatively difficult to detect, the subset of sensors that have a non-zero sensitivity to the test gas may have a low sensitivity and long temporal response, e.g., sampling time to reach threshold response Rt is relatively long. In this example, the threshold temporal response may be set to a relatively long period of time and threshold response may be set to a relatively low response R. In contrast, for a test gas with high concentrations of analytes of interest and/or analytes that are relatively simple to detect, the subset of sensors that have a non-zero sensitivity may be a large subset of the multiple gas sensors, where at least some of the subset of gas sensors have high sensitivity to the test gas and quick temporal response, e.g., sampling time to reach threshold response Rt is relatively short. In this example, the threshold response may be set to a relatively short period of time and threshold response may be set to a relatively high response R.

In some implementations, the proper subset of gas sensors is selected by selecting an optimized set of gas sensors that collectively have a best response to the multiple analytes of the test gas. Each individual gas sensor may be nonresponsive to one or more analytes of the multiple analytes, but overall can have a best response to a particular analyte of the multiple analytes.

In some implementations, selecting the proper subset of gas sensors depends in part on cost considerations, reliability of each type of gas sensors of the gas sensing array, and a repeatability requirement of the particular environment and application. In one example, an environment having safety critical aspects, e.g., toxic gases, redundancy of sensing can factor into a selection of the proper subset of gas sensors, where multiple sensors having a same sensor response can be selected.

In some implementations, selecting the proper subset of gas sensors includes selecting only the gas sensors of the proper subset of gas sensors to be included in a gas sensing apparatus, e.g., gas sensing apparatus 402, that is deployed in a particular test environment, e.g., a factory setting. Fewer than the total available number of gas sensors, e.g., the multi-modal array of gas sensors discussed in FIG. 1, are physically incorporated into the gas sensing apparatus 402 that is deployed in a test environment.

In some implementations, selecting the proper subset of gas sensors includes collected data from only the gas sensors of the proper subset of gas sensors for a gas sensing apparatus, e.g., gas sensing apparatus 402, that is deployed in a particular test environment, e.g., a factory setting. The total available number of gas sensors, e.g., the multi-modal array of gas sensors 108 discussed in FIG. 1, are physically incorporated into the gas sensing apparatus 402 that is deployed in the test environment, but sensing data, e.g., response data 118, is only collected from the proper subset of gas sensors.

Figure 8:
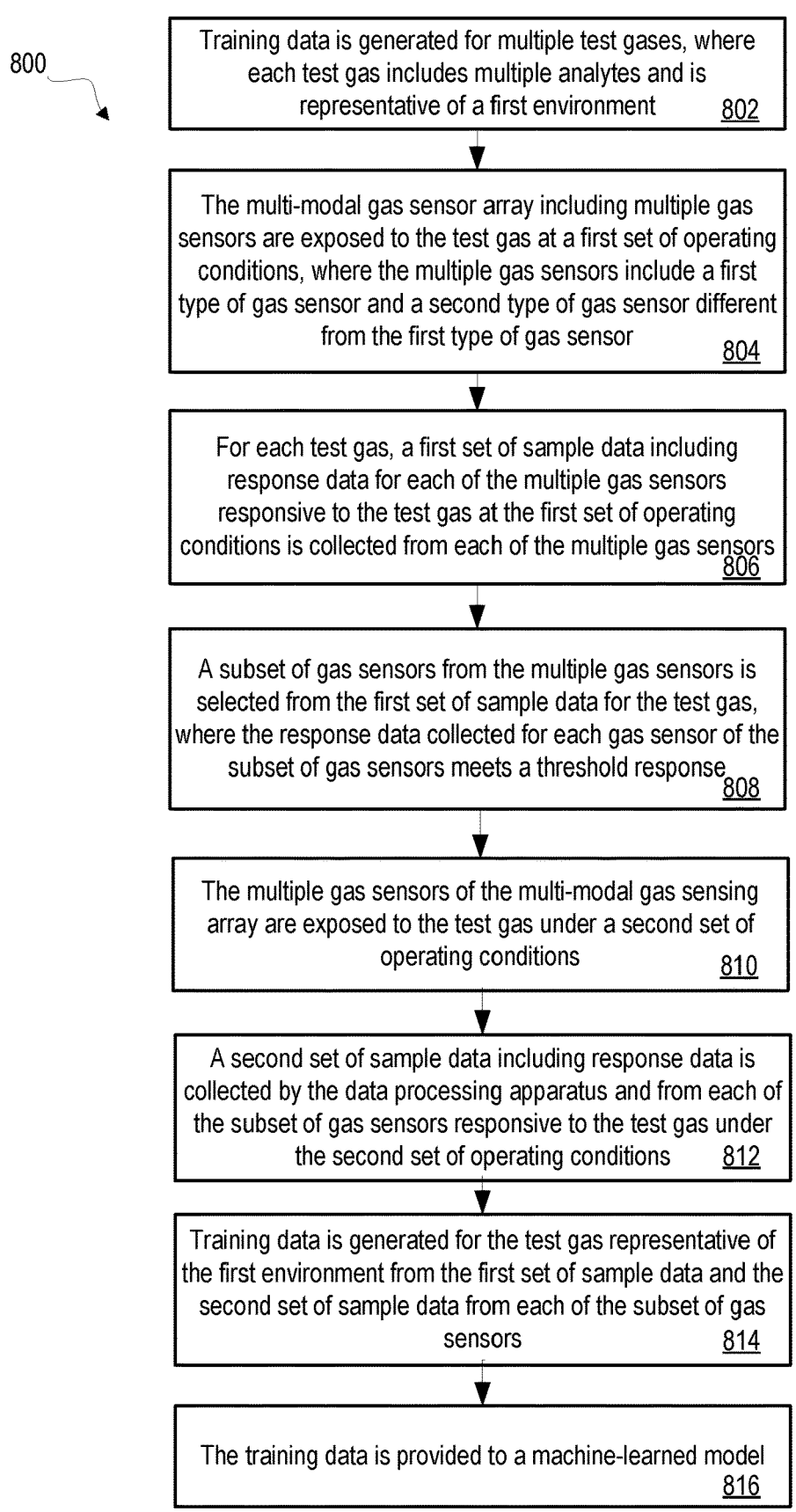

FIG. 8 is a flow diagram of an example process 800 of the e-nose gas sensing apparatus. The e-nose gas sensing apparatus 102 can be trained using system 100 including multiples test gases each including multiple known analytes from multiple gas sources in gas manifold 126.

Training data can be generated using system 100 and provided to train a machine-learned model which can then be deployed in a test environment to detect one or more analytes. Multiple sets of training data can be generated, where each set of training data can be customized for a particular test environment, e.g., a factory environment, an agricultural environment, a home environment, etc., such that the machine-learned model is trained to recognize a set of analytes that are relevant to the environment, e.g., process gases to a fabrication environment, and of importance to the particular environment, e.g., detecting toxic chemicals rather than inert chemicals. The process 800 described with reference to FIG. 8 is flexible such that the training data can be generated using a same gas sensing apparatus 102 for multiple different environments using a different set of known analytes and known concentrations of the analytes from gas sources 130.

Training data is generated for multiple test gases, where each test gas includes multiple analytes and is representative of a first environment (802). The first environment, e.g., an industrial environment, an agricultural environment, a residential environment, etc., can have a particular set of relevant analytes of interest and analytes not of interest, depending on the particulars of the environment. The test gases each include a particular composition of the set of multiple analytes, where the particular composition can include known concentrations of a subset of analytes of interest and analytes not of interest.

Training data is generated for each test gas including exposing the multi-modal gas sensor array including multiple gas sensors to the test gas at a first set of operating conditions, where the multiple gas sensors include a first type of gas sensor and a second type of gas sensor different from the first type of gas sensor (804). The first set of operating conditions includes a first concentration of a first analyte of interest of the multiple analytes and a second concentration of a second analyte not of interest of the multiple analytes. For example, the first concentration of the first analyte that is of interest is 0.2% of coffee and the second concentration of the second analyte that is not of interest is 1% of ethanol, where the first analyte and the second analyte are mixed with an inert gas, e.g., nitrogen, in the test gas.

Exposing the multi-modal gas sensor array includes flowing the test gas from the gas manifold 126 through gas inlet 110 into the environmental regulator 106. Within the environmental regulator 106, e.g., heating/cooling fins, the test gas is regulated to a particular temperature, e.g., as measured by temperature gauge 128 and monitored by environmental controller 124. The test gas is then provided to the array of gas sensors 108 and exhausted through gas outlet 112. A flow of the test gas within house 104 can be controlled by the environmental controller 124 and regulated in part using regulatory components of the gas manifold 126, e.g., flow meter 214, pressure regulator 202, by a negative pressure generated by fan 114 within the housing 104, or a combination thereof.

For each test gas, a first set of sample data including response data for each of the multiple gas sensors responsive to the test gas at the first set of operating conditions is collected by a data processing apparatus and from each of the multiple gas sensors (806). Response data 118 can be collected by data processing apparatus 116 from each of the multiple gas sensors 108 of the gas sensing apparatus 102. In some implementations, process 704A of FIG. 7B can be used to employ a sorbent tube pre-filter system 140 to analyze each test gas and obtain gas sensor response data.

The response data 118 can include multiple different formats of responses depending in part on a type of gas sensor 108 of the multiple different types of gas sensors. Formats of response data can include optical response data, e.g., from PID sensors, electrical resistivity data, e.g., from MOx sensors, and oxidation/reduction response data, e.g., from electrochemical sensors. In some implementations, the response data 118 includes a measure of electrical resistivity of the gas sensor over a period of time during the exposure to the test gas, e.g., for MOx gas sensors.

Additionally, annotation data 120, e.g., timestamps, temperature/humidity data, etc., delineating when the test gas is exposed to the gas sensors 108 can be recorded, e.g., when the test gas is provided from the environmental regulator 106 to the array of gas sensors 108. Further details of annotation data 120 are described in further detail with reference to FIGS. 3A-3C above.

Composition data 122 describing a particular composition of the test gas including the respective concentrations of one or more analytes of interest and one or more analytes not of interest in the test gas can be recorded for each test gas. The known analytes of interest and known analytes not of interest can be associated with the response data 118 generated by each gas sensor of the multi-modal array of gas sensors 108.

In some implementations, the known concentrations of known analytes can be used to label the response data 118, e.g., response outputs, of the multiple gas sensors. The labeled response data 118 can be provided to a machine-learned model for training. The labeled response data 118 can be processed, e.g., calibrated to a standard baseline, to ensure consistency between different sensing apparatuses 102 having a same design.

A subset of gas sensors from the multiple gas sensors is selected from the first set of sample data for the test gas, where the response data collected for each gas sensor of the subset of gas sensors meets a threshold response (808). As described above with reference to FIG. 7B, the subset of gas sensors can be selected, for example, based in part on each selected sensor meeting threshold of responsivity to the test gas. Additionally, the subset of gas sensors can be selected based in part on each selected sensor being below a threshold recovery period after termination of exposure of the selected gas sensor to the test gas.

In some implementations the multiple gas sensors are 38 or more gas sensors in the multi-modal array of gas sensors 108, where the subset of gas sensors includes fewer than all of the total number of gas sensors in the gas sensing apparatus 102. For example, the total number of gas sensors in the gas sensing apparatus 102 is 30 gas sensors of multiple different types, e.g., MOx sensors, PID sensors, electrochemical sensors, and the subset of selected gas sensors are 15 gas sensors, 20 gas sensors, or 8 gas sensors. The subset of gas sensors that is selected represents an optimized subset of the total available gas sensors in the gas sensing apparatus 102 for responding to the particular test gas under the first set of operating conditions.

The multiple gas sensors of the multi-modal gas sensing array are exposed to the test gas under a second set of operating conditions (810). The second set of operating conditions can differ from the first set of operating conditions based on sampling conditions, e.g., temperature/relative humidity, relative concentrations of the analytes in the test gas, and/or the set of one or more analytes of interest and analytes not of interest included in the test gas.

In some implementations, the second set of operating conditions includes a first concentration of a second analyte of interest of the multiple analytes and the second concentration of the analyte not of interest of the multiple analytes. Continuing the example from above, the second set of operating conditions can include a first concentration of a second analyte of interest, e.g., 0.1% vanilla, combined with 1% of ethanol as the analyte not of interest and mixed with the inert gas, e.g., nitrogen.

In some implementations, the second set of operating conditions includes a third concentration of the analyte of interest of the multiple analytes and a fourth concentration of the analytes not of interest of the multiple analytes, where the third concentration is different than the first concentration. Continuing the example from above, the third concentration of the analyte of interest can be 0.5% coffee and the fourth concentration of the analyte not of interest can be 5% of ethanol, where the two analytes are then mixed with an inert gas, e.g., nitrogen, to generate the test gas.

In another example, the third concentration of the analyte of interest can be 0.5% coffee and the fourth concentration of the analyte not of interest can be the same as the second concentration, e.g., 1% of ethanol, where the two analytes are then mixed with a purge gas, e.g., nitrogen, to generate the test gas.

In some implementations, prior to exposing the gas sensors to the test gas under the second set of operating conditions, the multiple gas sensors 108 are exposed to a purge gas, e.g., nitrogen or compressed clean dry air, for a period of time. The purge gas, e.g., gas source 130a depicted in FIG. 2, can be used to assist in shortening a recovery time of the sensors after exposure to the test gas, e.g., shorten P2 for gas sensor A in FIG. 3A, and/or to ensure that no remaining test gas is present within the housing 104 or gas manifold 126.

In some implementations, the period of time of exposure of the multiple gas sensors 108 to the purge gas can be an amount of time for each of the sensors to reach a baseline resistivity reading. The period of time of exposure can be selected based on a longest recovery time of all the respective recovery times for the multiple gas sensors 108. The period of time exposure of the multiple gas sensors 108 to the purge gas can be, for example, 1 minute, 5 minutes, 30 seconds, or the like.

A second set of sample data including response data is collected by the data processing apparatus and from each of the subset of gas sensors responsive to the test gas under the second set of operating conditions (812). Response data 118 can be collected by data processing apparatus 116 from only the selected subset of gas sensors 108 of the multiple gas sensors of the gas sensing apparatus 102 that were selected as responsive to the test gas under the first set of operating conditions in Step 808. The gas sensors 108 of the multiple gas sensors 108 not selected for inclusion in the subset of gas sensors 108 can be, for example, switched "off" during the sampling process. In another example, the gas sensors 108 not selected for inclusion in the subset of gas sensors 108 can be active, e.g., "on", during the sampling process but the data generated by those particular gas sensors may not be collected by the data processing apparatus 116.

Training data is generated for the test gas representative of the first environment from the first set of sample data and the second set of sample data from each of the subset of gas sensors (814). In some implementations, training data is generated by recording the captured response for each sensor to the test gas, an amount of time that the response was captured, e.g., a "sniff" time, as well as an amount of time that a baseline measurement of no gas exposure was recorded prior to exposure of the test gas and an amount of time that the response was captured after termination of the exposure to the test gas. In other words, training data includes sensor response as well as labeled timestamps denoting baseline measurement, exposure to test gas, and recovery measurement, e.g., as described with reference to FIGS. 3A-3C. Each labeled sensor response is produced for various test gases including varying compositions of analytes and concentrations of each analyte.

The process described with reference to Steps 802-814 can be repeated for multiple test gases, where each test gas is representative of the test environment. The multiple test gases can be selected based on a range of compositions and/or environmental conditions, e.g., temperature, over which the response of the gas sensors 108 are measured to generate the training data.

The training data is provided to a machine-learned model (816). A machine-learned model can be trained for each intended test environment using a particular set of test gases and environmental conditions. For example, a machine-learned model for an industrial applications can be different that a machine-learned model for a food production facility, where both sets of training data are generated using system 100 described with reference to FIG. 1.

In some implementations, training the machine-learned model using the training data can further include providing, to the subset of gas sensors, a particular test gas of the multiple test gasses under a third set of operating conditions. A third set of sample data is collected from each of the subset of gas sensors and provided to the machine-learned model. The machine-learned model determines characteristics descriptive of the particular test gas under the third set of operating conditions, e.g., determines the analytes included in the test gas and relative concentrations of each of the analytes included in the test gas. For example, the third set of operating conditions can include a fifth concentration of the analyte of interest, e.g., 0.6% of coffee, and a sixth concentration of the analyte not of interest, e.g., 1% of ethanol, where the two analytes are mixed with an inert gas, e.g., nitrogen, to generate the test gas under the third set of operating conditions.

In some implementations, the operating conditions of the first set of operating conditions, the second set of operating conditions, and the third set of operating conditions are defined as a particular temperature and relative humidity of the test gas and the gas sensors 108 when the test gas is exposed to the subset of gas sensors 108. For example, the first set of operating conditions can be 20 degrees C. at 10% humidity, the second set of operating conditions can be 40 degrees C. at 33% humidity, and the third set of operating conditions can be 35 degrees C. at 33% humidity.

In some implementations, determining characteristics descriptive of the test gas under the third set of operating conditions includes identifying, by the machine-learned model, a first concentration of a first analyte in the test gas under the third set of operating conditions.

Figure 9B:
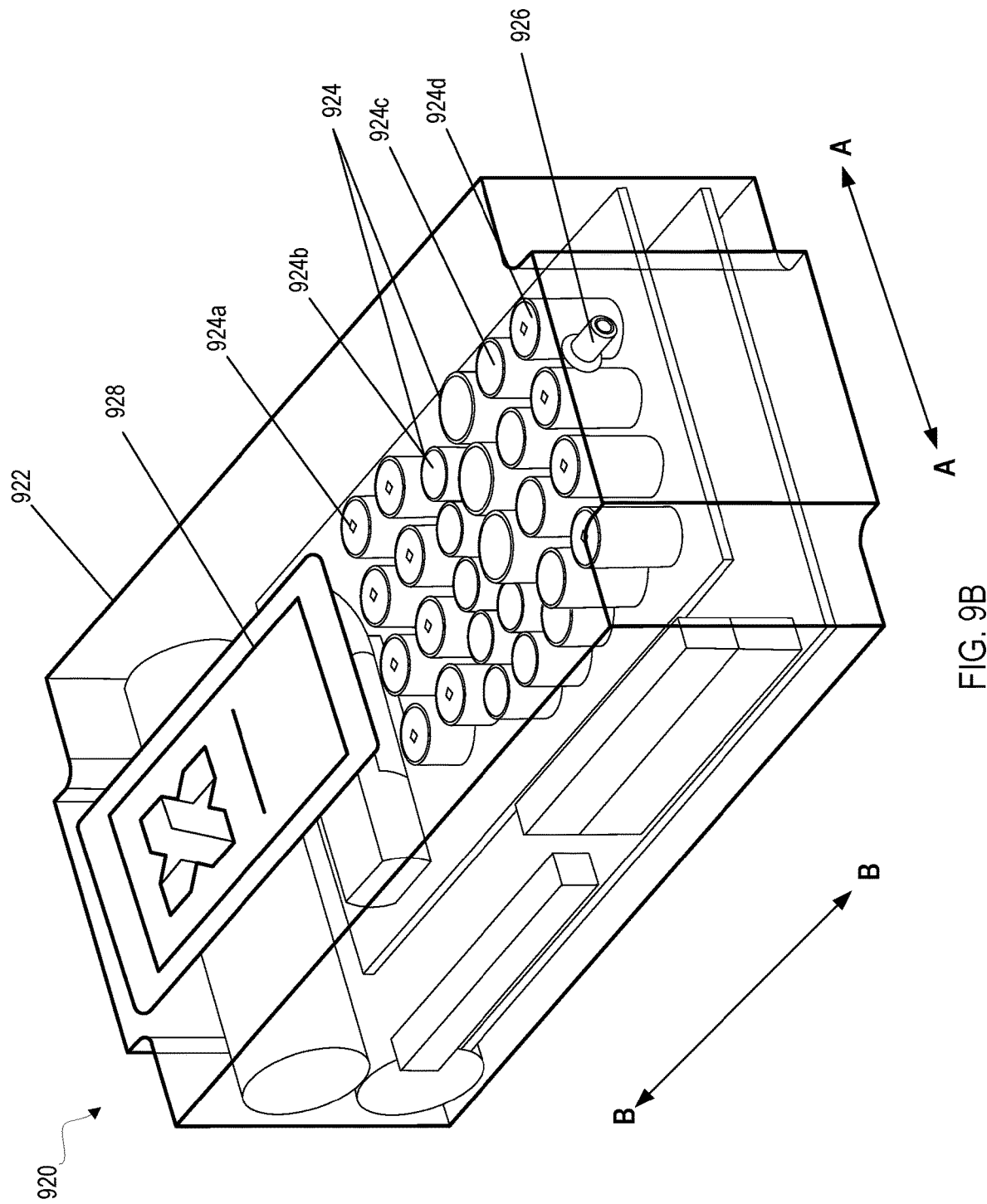

FIG. 9A-9D are schematics of example views of e-nose gas sensing apparatuses. FIG. 9A depicts an example exterior of an e-nose gas sensing apparatus 900, e.g., gas sensing apparatus 402. The gas sensing apparatus 900 can include housing 902, e.g., housing 104, enclosing the various components of the gas sensing apparatus 900. A gas inlet 904, e.g., gas inlet 110, can receive an unknown gas mixture, e.g., unknown gas mixture 404, and provide the unknown gas mixture to a multi-modal gas sensing array, e.g., a multi-modal array of gas sensors 108, within the housing 902. Gas sensing apparatus 900 can include a display 906, e.g., display 406, which can include a touchscreen. Display 906 can provide an intuitive user interface for receiving user instructions, e.g., run test, testing parameters, etc., and display information, e.g., information 408, to a user viewing the display 906.

A footprint, e.g., width and length, of the gas sensing apparatus 900 can be, for example, smaller than 2×4 inches, smaller than 10×12 inches, smaller than 20×20 inches, or the like. Though depicted in FIG. 9A as having a rectangular form factor, other form factors are possible, e.g., cylindrical form factor. In one example, the gas sensing apparatus 900 can have dimensions similar to a standard shoebox, e.g., 14×8×5 inches. In some implementations, a footprint of the gas sensing apparatus 900 can be fit to the dimensions of a silicon chip, e.g., on the order of 1 mm×1 mm×0.1 mm or smaller.

FIG. 9B depicts a perspective view, another example of an e-nose gas sensing apparatus 920 where a portion of the house 922 of the gas sensing apparatus 920 is transparent to view an interior of the apparatus 920. Gas sensing apparatus 920 including a multi-modal array of gas sensors 924, e.g., a multi-modal array of gas sensors 108. As depicted in FIG. 9B, a multi-modal array of gas sensors 924 includes multiple types of gas sensors 924a, 924b, 924c, and 924d. The multiple types of gas sensors can have different form factors, gas sensing mechanisms, operating parameters, or the like. The multi-modal array of gas sensors is described in further detail above with reference to FIGS. 1-6.

Gas sensing apparatus 920 includes a gas inlet 926, e.g., gas inlet 110, to receive an unknown gas mixture, e.g., unknown gas mixture 404, and provide the unknown gas mixture to a multi-modal gas sensing array 924. Gas sensing apparatus 920 can route the unknown gas mixture from the gas inlet 926 via internal tubing and/or fins to regulate the flow of the unknown gas mixture across the gas sensors 924. In some implementations, the gas sensing apparatus 920 includes heating fins or another temperature control component, e.g., as described with reference to the environmental regulator 106 in FIGS. 1 and 4.

In some implementations, gas sensing apparatus 920 includes a display 1028

Figure 9C:
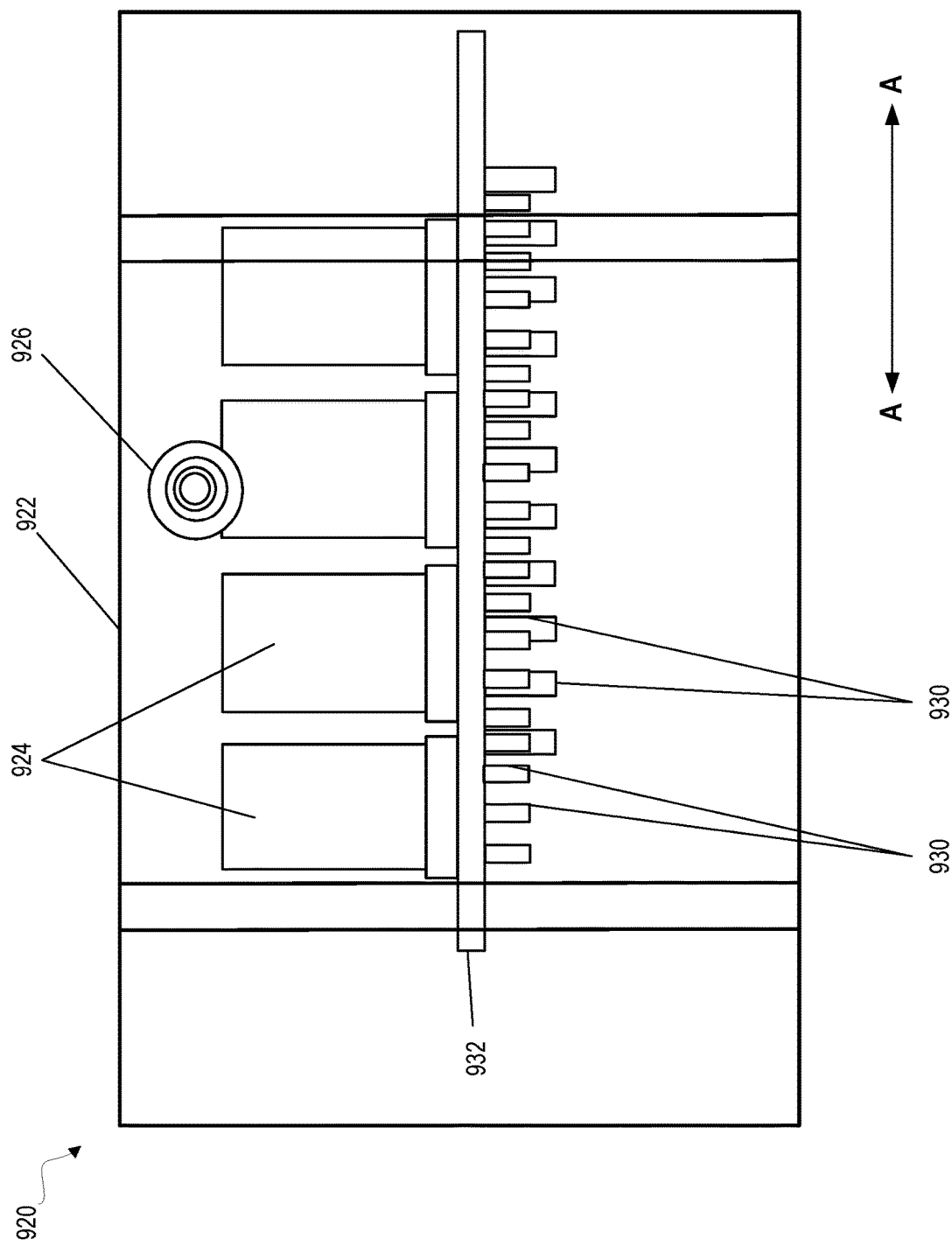

FIG. 9C depicts a side view of gas sensing apparatus 920 along axis A-A. Housing 922 is depicted as transparent to display the interior components of the gas sensing apparatus 920. Gas sensors 924 include respective circuitry 930, e.g., contacts or pins, and can be in physical and electrical contact with additional circuitry of a printed circuit board (PCB) 932. Additional electrical connections to the gas sensors 924 via circuitry 930 to a data processing apparatus, e.g., data processing apparatus 116, can be included (not shown).

Figure 9D:
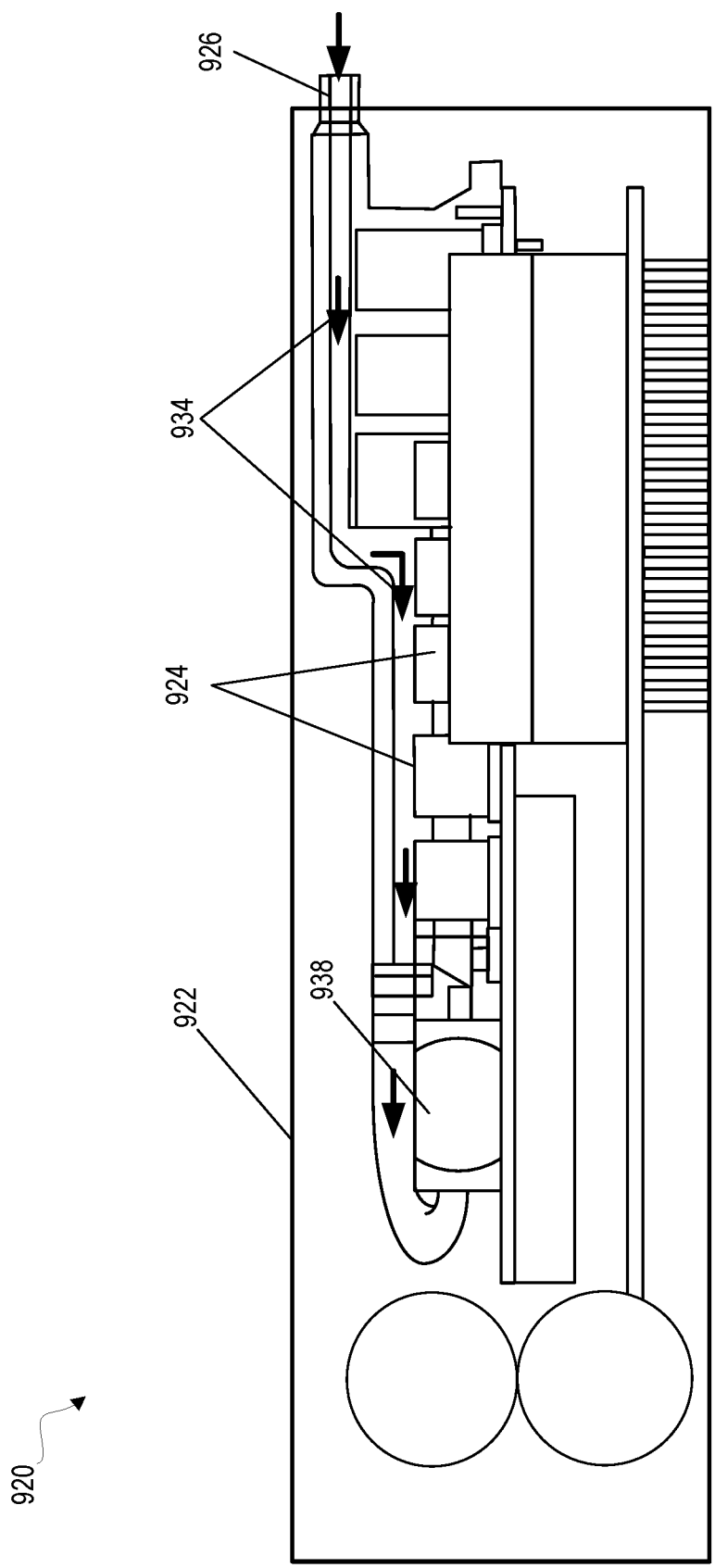

FIG. 9D depicts another side view of gas sensing apparatus 920 along axis B-B. Housing 922 is depicted as transparent to display the interior components of the gas sensing apparatus 920. Unknown gas mixture introduced at gas inlet 926 flows into the housing 922 and over the gas sensors 924, following a flow path indicated by 934. Gas mixture is purged through gas outlet 936, e.g., gas outlet 112. In some implementations, a fan, pump, or blower 938, e.g., fan 114, can provide a negative pressure within the housing 922 to facilitate a flow from the gas inlet 926 to a gas outlet (not pictured), e.g., gas outlet 112.

Figure 10:
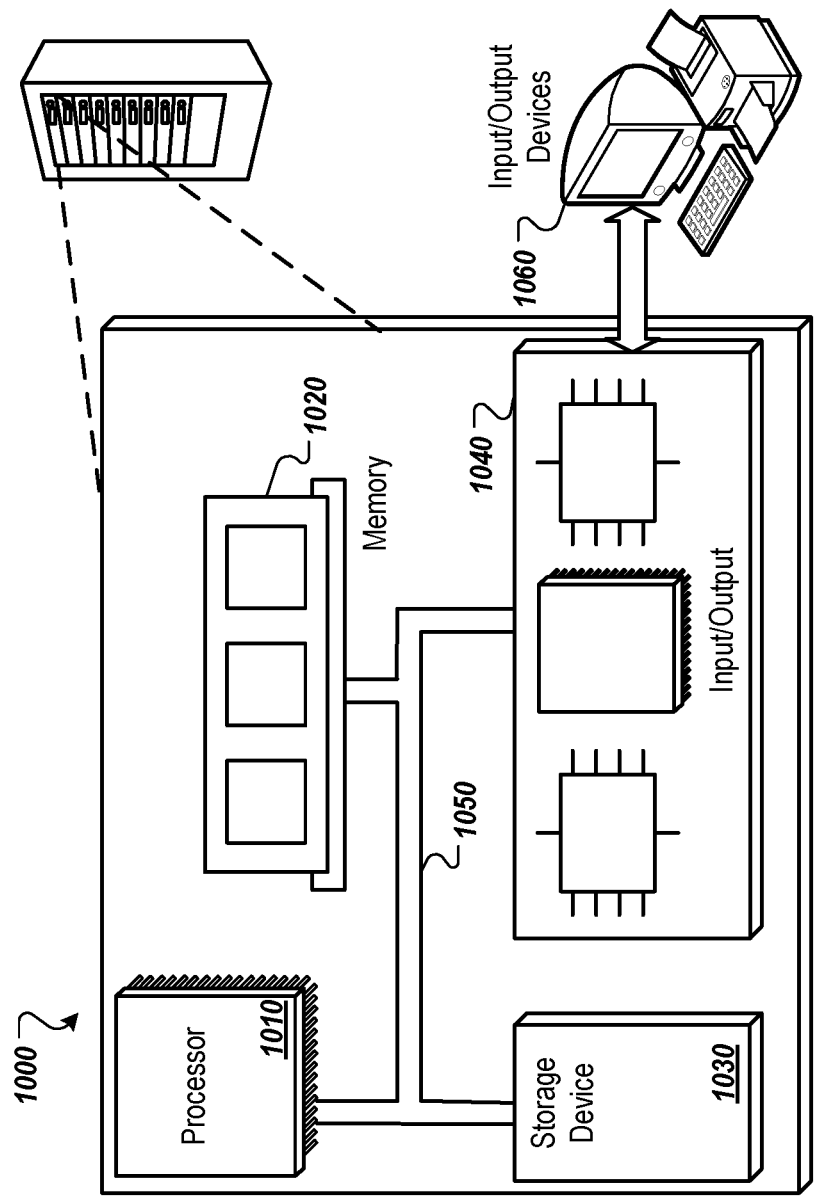
FIG. 10 is a block diagram of an example computer system.

FIG. 10 is a block diagram of an example computer system 1000 that can be used to perform operations described above. The system 1000 includes a processor 1010, a memory 1020, a storage device 1030, and an input/output device 1040. Each of the components 1010, 1020, 1030, and 1040 can be interconnected, for example, using a system bus 1050. The processor 1010 is capable of processing instructions for execution within the system 1000. In one implementation, the processor 1010 is a single-threaded processor. In another implementation, the processor 1010 is a multi-threaded processor. The processor 1010 is capable of processing instructions stored in the memory 1020 or on the storage device 1030.

The memory 1020 stores information within the system 1000. In one implementation, the memory 1020 is a computer-readable medium. In one implementation, the memory 1020 is a volatile memory unit. In another implementation, the memory 1020 is a non-volatile memory unit.

The storage device 1030 is capable of providing mass storage for the system 1000. In one implementation, the storage device 1030 is a computer-readable medium. In various different implementations, the storage device 1030 can include, for example, a hard disk device, an optical disk device, a storage device that is shared over a network by multiple computing devices (for example, a cloud storage device), or some other large capacity storage device.

The input/output device 1040 provides input/output operations for the system 1000. In one implementation, the input/output device 1040 can include one or more network interface devices, for example, an Ethernet card, a serial communication device, for example, a RS-232 port, and/or a wireless interface device, for example, a 802.11 card. In another implementation, the input/output device can include driver devices configured to receive input data and send output data to other input/output devices, for example, keyboard, printer and display devices 1060. Other implementations, however, can also be used, such as mobile computing devices, mobile communication devices, set-top box television client devices, etc.

Although an example processing system has been described in FIG. 10, implementations of the subject matter and the functional operations described in this specification can be implemented in other types of digital electronic circuitry, or in computer software, firmware, or hardware, including the structures disclosed in this specification and their structural equivalents, or in combinations of one or more of them.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, that is, one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, for example, a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, for example, an FPGA (field programmable gate array) or an ASIC (application-specific integrated circuit). The apparatus can optionally include, in addition to hardware, code that creates an execution environment for computer programs, for example, code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, for example, an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a Global Positioning System (GPS) receiver, or a portable storage device, for example, a universal serial bus (USB) flash drive, to name just a few.

Computer-readable media suitable for storing computer program instructions and data include all forms of non-volatile memory, media and memory devices, including by way of example semiconductor memory devices, for example, EPROM, EEPROM, and flash memory devices; magnetic disks, for example, internal hard disks or removable disks; magneto-optical disks; and CD-ROM and DVD-ROM disks.

To provide for interaction with a user, embodiments of the subject matter described in this specification can be implemented on a computer having a display device, for example, a CRT (cathode ray tube) or LCD (liquid crystal display) monitor, for displaying information to the user and a keyboard and a pointing device, for example, a mouse or a trackball, by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of messages to a personal device, for example, a smartphone that is running a messaging application and receiving responsive messages from the user in return.

Data processing apparatus for implementing machine learning models can also include, for example, special-purpose hardware accelerator units for processing common and compute-intensive parts of machine learning training or production, that is, inference, workloads.

Machine learning models can be implemented and deployed using a machine learning framework, for example, a TensorFlow framework, a Microsoft Cognitive Toolkit framework, an Apache Singa framework, or an Apache MXNet framework.

Embodiments of the subject matter described in this specification can be implemented in a computing system that includes a back-end component, for example, as a data server, or that includes a middleware component, for example, an application server, or that includes a front-end component, for example, a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, for example, a communication network. Examples of communication networks include a local area network (LAN) and a wide area network (WAN), for example, the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, for example, an HTML page, to a user device, for example, for purposes of displaying data to and receiving user input from a user interacting with the device, which acts as a client. Data generated at the user device, for example, a result of the user interaction, can be received at the server from the device.

While this specification contains many specific implementation details, these should not be construed as limitations on the scope of any features or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A gas sensing apparatus comprising:
a sample inlet;
a first sorbent tube and a second sorbent tube each in fluidic communication with the sample inlet, wherein the first sorbent tube is sensitive to a first set of gas analytes and the second sorbent tube is sensitive to a second, different set of gas analytes;
an array of gas sensors housed in a chamber that is in fluidic communication with the first sorbent tube and the second sorbent tube, wherein the first sorbent tube and the second sorbent tube are located between the sample inlet and the chamber housing the array of gas sensors; and
a desorption system configured to selectively desorb and direct contents from the first sorbent tube into the chamber housing the array of gas sensors at a first sampling time and selectively desorb and direct contents from the second sorbent tube into the chamber housing the array of gas sensors at a second, different time.

2. The gas sensing apparatus of claim 1, wherein the desorption system comprises a first flow path between the first sorbent tube and the chamber housing the array of gas sensors, and a second flow path between the second sorbent tube and the chamber containing the array of gas sensors, and
wherein the gas sensing system further comprises:

a pump in fluidic communication with the first sorbent tube and the second sorbent tube; and a processing system configured to control operations of the gas sensing system and to perform operations comprising:

causing the pump to draw a gas sample through the first sorbent tube and the second sorbent tube;

causing the desorption system to open the first flow path;

causing the desorption system to desorb a content of the first sorbent tube into the chamber through the first flow path;

obtaining, from the array of gas sensors, first sensor response data responsive to the content of the first sorbent tube;

causing the desorption system to isolate the first flow path;

causing the desorption system to open the second flow path;

causing the desorption system to desorb a content of the second sorbent tube into the chamber; and obtaining, from the array of gas sensors, second sensor response data responsive to the content of the second sorbent tube.

3. The gas sensing apparatus of claim 2, wherein the operations further comprise:

obtaining data identifying the first set of gas analytes that the first sorbent tube is sensitive to; and identifying, based on the data identifying the first set of gas analytes and the first sensor response data, at least one analyte present in the gas sample.

4. The gas sensing apparatus of claim 3, wherein identifying the at least one analyte present in the gas sample comprises comparing the first sensor response data with training data from sensor response curves associated with the first set of gas analytes.

5. The gas sensing apparatus of claim 2, wherein causing the desorption system to desorb the content of the first sorbent tube comprises activating a desorption mechanism associated with the first sorbent tube.

6. The gas sensing apparatus of claim 5, wherein activating a desorption mechanism associated with the first sorbent tube comprises activating a heater proximate to the first sorbent tube.

7. The gas sensing apparatus of claim 1, wherein the array of gas sensors includes a multi-modal array of gas sensors of different types.

8. The gas sensing apparatus of claim 1, wherein the array of gas sensors comprises a first array of gas sensors housed in a first chamber and a second array of different gas sensors house in a second chamber, and wherein the desorption system is configured to direct contents from the first sorbent tube to the first chamber and to direct contents from the second sorbent tube to the second chamber.

9. The gas sensing apparatus of claim 1, wherein the desorption system is configured to flush the chamber after desorbing and directing the contents from one of the first or second sorbent tube into the chamber.

10. The gas sensing apparatus of claim 1, wherein the first sorbent tube is removable from the gas sensing system.

11. A method of detecting analytes in gas, the method comprising:

drawing a gas sample through a first sorbent tube and a second sorbent tube of a gas sensing system, wherein the first sorbent tube is sensitive to a first set of gas analytes and the second sorbent tube is sensitive to a second, different set of gas analytes, and wherein the first sorbent tube and the second sorbent tube are located between a sample inlet and a chamber containing an array of gas sensors;

opening a first flow path between the first sorbent tube and the chamber containing the array of gas sensors;

selectively desorbing a content of the first sorbent tube into the chamber through the first flow path at a first sampling time;

obtaining, from the array of gas sensors, first sensor response data responsive to the content of the first sorbent tube;

isolating the first flow path;

opening a second flow path between the second sorbent tube and the chamber containing the array of gas sensors;

selectively desorbing a content of the second sorbent tube into the chamber through the second flow path at a second, different sampling time; and obtaining, from the array of gas sensors, second sensor response data responsive to the content of the second sorbent tube.

12. The method of claim 11, wherein the array of gas sensors includes a multi-modal array of gas sensors of different types.

13. The method of claim 11, wherein the array of gas sensors comprises a first array of gas sensors housed in a first chamber and a second array of different gas sensors house in a second chamber, and wherein the first flow path directs the content from the first sorbent tube to the first chamber and the second flow path directs contents from the second sorbent tube to the second chamber.

14. The method of claim 11, further comprising flushing the chamber after desorbing the content of the first sorbent tube into the chamber through the first flow path.

15. The method of claim 11, wherein the first sorbent tube is removable from the gas sensing system.

16. The method of claim 11, further comprising:

obtaining data identifying the first set of gas analytes that the first sorbent tube is sensitive to; and identifying, based on the data identifying the first set of gas analytes and the first sensor response data, at least one analyte present in the gas sample.

17. The method of claim 16, wherein identifying the at least one analyte present in the gas sample comprises comparing the first sensor response data with training data from sensor response curves associated with the first set of gas analytes.

18. The method of claim 11, wherein desorbing the content of the first sorbent tube comprises activating a desorption mechanism associated with the first sorbent tube.

19. The method of claim 18, wherein activating a desorption mechanism associated with the first sorbent tube comprises activating a heater proximate to the first sorbent tube.

20. A gas sensing system comprising:

a sorbent tube array comprising a first sorbent tube and a second sorbent tube, each in fluidic communication with one or more gas sensors, wherein the first sorbent tube is sensitive to a first set of gas analytes and the second sorbent tube is sensitive to a second, different set of gas analytes, wherein the sorbent tube array is located between a sample inlet and a chamber containing the one or more gas sensors;

at least one processor in communication with the gas sensors; and a data store coupled to the at least one processor having instructions stored thereon which, when executed by the at least one processor, causes the at least one processor to perform operations comprising:
  causing a gas sample to be drawn through the first sorbent tube and the second sorbent tube;
  opening a first flow path between the first sorbent tube and the chamber containing the gas sensors;
  causing a content of the first sorbent tube to be selectively desorbed into the chamber through the first flow path at a first sampling time;
  obtaining, from the gas sensors, first sensor response data responsive to the content of the first sorbent tube;
  causing the first flow path to be isolated;
  opening a second flow path between the second sorbent tube and the chamber containing the gas sensors;
  causing a content of the second sorbent tube to be selectively desorbed into the chamber through the second flow path at a second, different sampling time; and
  obtaining, from the gas sensors, second sensor response data responsive to the content of the second sorbent tube.

* * * * *